United States Patent [19]

Leikhim et al.

[11] 4,013,573
[45] Mar. 22, 1977

[54] CARRIER GRANULE FOR AN ORGANOSILANE

[75] Inventors: John W. Leikhim, Cincinnati; Edward J. Maguire, Jr., Forest Park; David C. Heckert, Oxford; David M. Watt, Jr., Cincinnati, all of Ohio

[73] Assignee: The Procter & Gamble Company, Cincinnati, Ohio

[22] Filed: Apr. 22, 1975

[21] Appl. No.: 570,536

[52] U.S. Cl. .............................. 252/89 R; 252/96; 252/142; 260/448.2 N; 260/448.8 R; 427/212; 427/219; 427/220; 427/221

[51] Int. Cl.² ........................................ C11D 1/00

[58] Field of Search ............... 252/89, 142, 99; 427/212, 219, 220, 221; 260/448.2 N, 448.8 R

[56] References Cited

UNITED STATES PATENTS 3,624,120   11/1971   Yetter .................... 260/448.2 N

*Primary Examiner*—Mayer Weinblatt
*Attorney, Agent, or Firm*—C. R. Wilson; R. B. Aylor; T. H. O'Flaherty

[57] ABSTRACT

A carrier granule containing an inert inner core and a coating of an organosilane and water-soluble or water-dispersible, normally solid, nonionic material. The organosilane is stabilized within the carrier granule and can be included in moisture-containing, highly alkaline or electrolyte-containing compositions, e.g. detergent compositions.

23 Claims, No Drawings

CARRIER GRANULE FOR AN ORGANOSILANE

BACKGROUND OF THE INVENTION

This invention relates to a carrier granule containing an organosilane compound. The carrier granule can be used in detergent compositions which are intended for use on hard, i.e. metallic and vitreous surfaces. The inclusion of the hereindescribed organosilane compound in the carrier granule assures its stability when added to compositions which contain moisture and have a high pH and/or electrolyte content.

Copendng commonly assigned Patent Applications entitled "Organosilane-Containing Detergent Composition" and "Organosilane-Containing Anionic Detergent Composition" by David C. Heckert and David M. Watt, Jr., U.S. Ser. No. 570,534, filed Apr. 22, 1975, and U.S. Ser. No. 570,533 filedApr. 22, 1975 respectively disclose detergent compositions containing an organosilane compound. The organosilane compound is included in the detergent compositions for its soil release benefits. That is, when hard surfaces are washed with such a detergent composition, a thin polymeric layer of the organosilane compound is deposited on said surfaces. When the surfaces are thereafter soiled, the soil adheres less tenaciously to the surface as a result of this polymeric coating.

Detergent compositions normally contain water and have a relatively high pH, i.e. above pH 7. Unfortunately, such conditions affect the efficacy of the organosilane compound for its intended function; that is, the organosilane compound is likely to excessively polymerize prematurely. As a result of this, the polymerized organosilane compound is not as efficient as the unpolymerized organosilane or its oligomer in properly depositing itself upon subsequently washed hard surfaces.

It has now been found that the organosilane compounds can be made more stable in a detergent composition context by forming a carrier granule containing said organosilane.

It is another object of this invention to provide a method whereby an organosilane compound can be included in a detergent composition for prolonged time intervals without the organosilane compound being significantly altered in form.

It is another object of this invention to provide a carrier granule containing an organosilane compound and a nonionic material.

Still another object of this invention is to provide a detergent composition containing an organosilane in a form which can withstand moisture and high alkalinity and/or electrolytes.

These and other objects will become apparent from the description to follow.

As used herein, all percentages and ratios are by weight unless otherwise indicated.

SUMMARY OF THE INVENTION

A carrier granule containing an organosilane compound which comprises an inner core of an inert, organic or inorganic material whose surface has thereon an organosilane and a water-soluble or water-dispersible, normally solid, nonionic material consisting essentially of
a. from 25% to 95% of a inert organic or inorganic granular material serving as the inner core;
b. from 2% to 50% of a organosilane having the formula

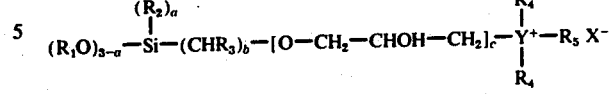

or is a siloxane oligomer thereof wherein $R_1$ is an alkyl group containing 1 to 4 carbon atoms, $$(CH_3)_3Si \text{ or } Z(OC_xH_{2x})_m$$

where $x$ is 2 to 4, $m$ is 1 to 20, and $Z$ is hydrogen, an alkyl group containing 1 to 18 carbons or an acyl group containing 1 to 18 carbon atoms; $R_2$ is an alkyl group containing 1 to 18 carbon atoms; $a$ is 0 to 2; $R_3$ is hydrogen or an alkyl group containing 1 to 18 carbon atoms; $b$ is 1 to 3; $c$ is 0 or 1; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and $Z$ are as defined above, or oxygen provided only one $R_4$ is oxygen; $R_5$ is an alkyl, aryl or arylalkyl group containing 1 to 22 carbon atoms; X is halide; and Y is nitrogen, sulfur or phosphorus; and
c. from 3% to 70% of a water-soluble or water-dispersible, normally solid nonionic material wherein the organosilane and nonionic material are on the surface of the inner core.

DETAILED DESCRIPTION OF THE INVENTION

The carrier granule of this invention contains an inert organic or inorganic inner core and, as an outer coating, an organosilane and water-soluble or water-dispersible, normally solid, nonionic material. The inert organic or inorganic inner core, organosilane and nonionic materials are described in the succeeding paragraphs.

Inert organic or inorganic materials serve as the inner core of the carrier granule. Suitable materials are water soluble or -dispersible, and inert to the organosilane. Preferably they are also non-hygroscopic, non-electrolytic and non-alkaline. Examples of such materials include flaked polyethylene glycol having a molecular weight of from 4000 to 30,000 sodium sulfate, sulfite, bicarbonate, acetate and anhydrous citrate, and sucrose.

It should be understood the above listing or organic and inorganic materials is merely illustrative and not limiting. The only criteria for selecting a material as the inner core of the carrier granule is that it be inert to the organosilane, and water-soluble or -dispersible.

The inner core material represents from 25 % to 95 %, preferably 50 % to 75 % of the carrier granule. Surrounding it are the organosilane and the normally solid nonionic material.

The organosilane has the formula

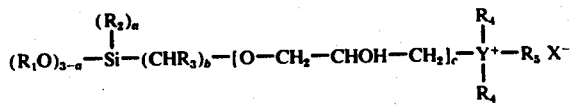

or is a siloxane oligomer thereof wherein $R_1$ is an alkyl group containing 1 to 4 carbon atoms, $(CH_3)_3Si$ or $Z(OC_xH_{2x})_m$ where $x$ is 2 to 4, $m$ is 1 to 20, and Z is hydrogen, an alkyl group containing 1 to 18 carbon atoms or an acyl group containing 1 to 4 carbon atoms; $R_2$ is an alkyl group containing 1 to 18 carbon atoms; $a$ is 0 to 2; $R_3$ is hydrogen or an alkyl group containing 1 to 18 carbon atoms; $b$ is 1 to 3; $c$ is 0 or 1; $R_4$ is an alkyl, aryl or arylalkyl group containing 1 to 12 carbon atoms, a carboxy-substituted alkyl group containing 1 to 4 carbon atoms, $(C_xH_{2x}O)_mZ$ where $x$, $m$ and Z are as defined above, or oxygen provided only one $R_4$ is oxygen; $R_5$ is an alkyl, aryl or arylalkyl group containing 1 to 22 carbon atoms; X is halide; and Y is nitrogen, sulfur or phosphorus. Preferably X is chloride or bromide and b is 1.

It should be understood that the $R_4$ in the above formula and the formulae to follow may be the same or different. It should further be understood that when Y is S, there will be only one $R_4$ substituent. Also, when one $R_4$ is oxygen or, under acidic conditions, the anion of a carboxylic acid substituted alkyl, the counter ion $X^-$ is not extant. The 1 to 4 carbon atoms in the carboxy-substituted alkyl group is inclusive of the carboxyl group. The aryl or arylalkyl groups of $R_4$ and $R_5$ contain 6 to 12 carbon atoms and 6 to 22 carbon atoms, respectively.

Classes of organosilane compounds and their preparation which fit the above description follow.

I. $(R_1O)_3-Si-(CH_2)_b-\overset{R_4}{\underset{R_4}{Y^+}}-R_5\ X^-$ wherein $R_1$ is a $C_{1-4}$ alkyl group, $b$ is from 1–3, $R_4$ is a $C_{1-12}$ alkyl, aryl or arylalkyl group, a carboxy-substituted $C_{1-4}$ alkyl group, $(C_xH_{2x}O)_mZ$ where $x$ is 2–4, $m$ is 1–20, and Z is hydrogen, a $C_{1-28}$ alkyl group or a $C_{1-4}$ acyl group, or oxygen provided only one $R_4$ is oxygen, $R_5$ is a $C_{4-22}$ alkyl, aryl or arylalkyl group, X is halide, and Y is N, S or P.

When $b$ is 3 and $R_4$ is a $C_{1-12}$ alkyl, aryl or arylalkyl group, the class of compounds represented by Formula I is prepared by the following route:

The trihalosilane (where the halogen is chlorine or bromine) is reacted with the allyl chloride at about 100° C. for from 4 to 10 hours in the presence of a catalyst, e.g., chloroplatinic acid or platinum. The resultant gammahalopropyltrihalosilane is reacted with a lower alcohol to produce the gamma-halopropyltrialkoxysilane. At least three equivalents of alcohol per equivalent of halopropyltrihalosilane are added slowly to the silane. The gamma-halopropyltrihalosilane may be dissolved in a inert solvent, preferably hexane or pentane. (See W. Noll, "Chemistry and Technology of Silanes", Academic Press, New York, 1968, page 81 for the alcoholysis of halosilanes.) One equivalent of the gamma-halopropyltrialkoxysilane is reacted with one equivalent of the tertiary amine, tertiary phosphine, or dialkysulfide to produce the organosilane. An inert solvent, preferably of high dielectric constant, may be used. The reaction is carried out at temperatures of from 40° C. to 120° C. and a time of 2 to 20 hours for the reaction of the bromopropyltrialkoxysilane and 120° C. to 150° C. for 2 to 20 hours for the reaction of the chloropropyltrialkoxysilane.

The compounds of Formula I when at least one $R_4$ is a carboxy-substituted $C_{1-4}$ alkyl group are prepared in the same manner except for the last reaction step. Here, a tertiary amine, tertiary phosphine or dialkylsulfide having a carboxy-containing alkyl group(s) is reacted with the alpha, beta or gamma-haloalkyltrialkoxysilane at 50° C. to 200° C. for 2 hours to 20 hours. Such carboxy-substituted tertiary amines, tertiary phosphines, and dialkylsulfides are produced by reacting $R_4YHR_5$ or $HYR_5$ (where Y is sulfur)

with $X(CH_2)_{1-4}COOH$ in the presence of base at elevated temperatures, e.g. 59° C. to 150° C.

The compounds of Formula I when at least one $R_4$ is $(C_xH_{2x}O)_mZ$ with $x$, $m$ and Z as defined above are produced in the manner given above except for the last reaction step. Thus, alpha- beta- and gamma-haloalkyltrialkoxysilane is reacted with a tertiary amine, tertiary phosphine, or dialkylsulfide where at least one substituent is $(C_xH_{2x}O)_mZ$ The reaction takes place at a temperature of 50° C. to 200° C. and a time of from 2 to 10 hours.

$X_3SiH + CH_2=CHCH_2X \longrightarrow X_3Si(CH_2)_3X$
(trihalosilane) (allyl halide) (gamma-halopropyltrihalosilane)

$X_3Si(CH_2)_3X + 3R_1OH \longrightarrow (R_1O)_3Si(CH_2)_3X + 3HX$
(alcohol) (gamma-halopropyltrialkoxysilane)

$(R_1O)_3Si(CH_2)_3X + (R_4)_3\ or\ _2YR_5 \longrightarrow (R_1O)_3Si(CH_2)_3\overset{R_4}{\underset{R_4}{Y^+}}-R_5\ X^-$
(tertiary amine, tertiary phosphine, or dialkylsulfide)

(gamma-trialkylammoniopropyltrialkoxysilane halide gamma-trialkylphosphoniopropyltrialkoxysilane halide, or gamma-dialkylsulfoniopropyltrialkoxysilane halide)

Compounds of Formula I when one $R_4$ is oxygen are prepared by following the reactions outlined above up to the last reaction step. At this point, a dialkyl amine, dialkyl phosphine or alkylthiol is reacted with the halosilane at 50° C. to 200° C. for from 4 to 10 hours and then with base to produce an intermediate tertiary amine, phosphine, or dialkyl sulfide. These intermediates are then reacted with $H_2O_2$ at 20° C. to 100° C. or preferably $O_3$ in an inert solvent at −80° C. to 20° C. to yield the organosilane.

When $b$ is 2 in Formula I, a trihalovinylsilane of formula $$X_3SiCH=CH_2$$

(which is commercially available) is reacted with hydrogen bromide in the presence of peroxide or light to produce a beta-haloethyltrihalosilane. This compound is reacted with an alcohol and thereafter with an appropriate amine, phosphine, or sulfide in the manner discussed above for the preparation of the compounds of Formula I when $b$ is 3.

When $b$ is 1 in Formula I, the starting reactant is a commercially available trihalomethylsilane of formula $$X_3SiCH_3.$$

This silane is reacted with chlorine or, preferably a half mole of bromine and a half mole of chlorine in the presence of light (such as provided by an ordinary tungsten or fluorescent lamp). The resultant alpha-halomethyltrihalosilane is reacted with an alcohol and thereafter an appropriate amine, phosphine or sulfide in the manner discussed above with the compounds of Formula I when $b$ is 3.

Examples of compounds illustrative of compounds of Formula I follow:

$(CH_3O)_3SiCH_2N^+(CH_3)_2C_{16}H_{33}$ $Cl^-$
$(C_2H_5O)_3SiCH_2N^+(CH_3)_2C_6H_5$ $Cl^-$
$(C_2H_5O)_3Si(CH_2)_3N^+(C_2H_5)_2C_{10}H_{21}$ $Br^-$
$(C_3H_7O)_3SiCH_2N^+(C_3H_7)_2C_6H_4CH_3$ $Br^-$
$(C_4H_9O)_3Si(CH_2)_2N^+(C_2H_5)(CH_2C_6H_5)_2$ $Cl^-$
$(CH_3O)_3SiCH_2P^+(C_2H_5)_2C_{12}H_{25}$ $Cl^-$
$(C_2H_5O)_3Si(CH_2)_3P^+(C_4H_9)_2C_6H_5$ $Cl^-$
$(C_3H_7O)_3Si(CH_2)_2S^+(CH_3)C_6H_5$ $Cl^-$
$(CH_3O)_3SiCH_2CH_2S^+(C_2H_5)$ $C_{16}H_{33}$ $Br^-$
$(CH_3O)_3SiCH_2N^+(C_2H_4COOH)_2C_{10}H_{21}$ $Br^-$
$(C_2H_5O)_3Si(CH_2)_3N^+(CH_2COOH)(CH_3)$ $C_{12}H_{25}$ $Cl^-$
$(C_2H_5O)_3Si(CH_2)_2P^+(C_3H_6COOH)$ $(C_2H_5)$ $C_{10}H_{21}$ $Cl^-$
$(C_4H_9O)_3SiCH_2S^+(C_3H_6COOH)C_6H_{13}$ $Br^-$
$(CH_3O)_3SiCH_2N$ $(C_2H_4OH)_2C_{18}H_{37}$ $Cl^-$
$(C_4H_9O)_3Si(CH_2)_3P^+(C_3H_6OH)_2C_6H_4CH_3$ $Cl^-$
$(C_2H_5O)_3SiCH_2S^+(C_3H_6OH)C_{14}H_{29}$ $Cl^-$
$(CH_3O)_3SiCH_2N^+(O)^-(CH_3)$ $C_{14}H_{29}$
$(C_2H_5O)_3Si(CH_2)_3P^+(O)^-(C_2H_5)C_{12}H_{25}$
$(C_2H_5O)_3Si(CH_2)_2S^+(O)^-C_{10}H_{21}$
$(CH_3O)_3SiCH_2N^+[(C_2H_4O)_3H](CH_3)C_8H_{17}$ $Cl^-$
$(CH_3O)_3Si(CH_2)_2N^+[(C_4H_8O)_{15}CH_3](CH_3)C_6H_{13}$
$(C_2H_5O)_3Si(CH_2)_3N^+[(C_2H_4O_6H]_2C_{10}H_{21}$ $Cl^-$
$(CH_3O)_3SiCH_2N^+[(C_2H_4O)_3COCH_3]_2C_8H_{17}$ $Cl^-$
$(C_3H_7O)_3SiCH_2P^+[(C_3H_6O)_{12}H]_2CH_2C_6H_5$ $Cl^-$
$(C_4H_9O)_3Si(CH_2)_3P^+[(C_2H_4O)_4C_4H_9]CH_3C_4H_9$ $Br^-$
$(CH_3O)_3Si(CH_2)_2P^+[(C_2H_4O)_5COC_2H_5]_2C_4H_9$ $Br^-$
$(CH_3O)_3SiCH_2S^+[(C_2H_4O)_5H]C_{10}H_{21}$ $Cl^-$
$(C_2H_5O)_3Si(CH_2)_2S^+[(C_3H_6O)_8C_3H_7]C_4H_9$ $Br^-$
$(CH_3O)_3Si(CH_2)_3S^+[(C_2H_4O)_{12}$ $COC_4H_9]C_{12}H_{25}$ $Cl^-$

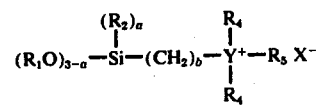

II.

where $R_1$ is a $C_{1-4}$ alkyl group, $R_2$ is a $C_{1-18}$ alkyl group $a$ is 1 or 2, $b$ is 1–3, $R_4$ is a $C_{1-12}$ alkyl, aryl or arylalkyl group, a carboxy-substituted $C_{1-4}$ alkyl group, $$(C_xH_{2x}O)_mZ$$

where $x$ is 2–4, $m$ is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

The compounds of Formula II are prepared in a manner similar to the preparation of the compounds of Formula I except for the fact that the starting reactants (when b is 1, 2, or 3) all have a $C_{1-18}$ alkyl group or two $C_{1-18}$ alkyl groups attached to the Si atom in place of a halogen atom(s). The starting reactant is commercially available when $R_2$ is $CH_3$. When $R_2$ is $C_2H_5$ or greater, the compound is prepared by reacting a silane with an appropriate olefin. Thus, $$X_{3-a}SiH_{1+a}$$

is reacted with a $C_2$ to $C_{18}$ olefin to obtain the desired starting reactant. The remaining reaction steps and conditions for producing the desired organosilane of Formula II are essentially the same as for producing the compounds of Formula I.

Examples of compounds of Formula II are:

$(CH_3O)_2CH_3SiCH_2N^+(CH_3)_2C_{12}H_{25}$ $Cl^-$
$(C_2H_5O)_2C_6H_{13}Si(CH_2)_2N^+(CH_3)_2C_{18}H_{37}$ $Cl^-$
$(C_3H_7O)(C_3H_7)_2Si(CH_2)_3N^+(C_2H_5)_2C_{10}H_{21}$ $Cl^-$
$(CH_3O)(CH_3)_2SiCH_2P^+(CH_3)_2C_{10}H_{21}$ $Cl^-$
$(C_3H_7O)_2C_{10}H_{21}Si(CH_2)_2S^+(C_4H_9)C_6H_{12}C_6H_5$ $Cl^-$
$(CH_3O)_2C_{16}H_{33}Si(CH_2)_3N^+(C_2H_4COOH)(CH_3)C_4H_9$ $Cl^-$
$(C_2H_5O)(CH_3)_2Si(CH_2)_2P^+(CH_2COOH)_2C_{10}H_{21}$ $Cl^-$
$(C_3H_7O)_2CH_3SiCH_2S^+(C_3H_6COOH)C_6H_{13}$ $Cl^-$
$(CH_3O)_2CH_3SiCH_2N^+(C_2H_4OH)_2C_{18}H_{37}$ $Cl^-$
$(C_3H_7O)(CH_3)_2SiCH_2P^+(C_3H_6OH)(C_4H_9)_2$ $Br^-$
$(C_4H_9O)_2CH_3Si(CH_2)_3S^+(C_3H_6OH)CH_3$ $Br^-$
$(CH_3O)_2CH_3SiCH_2N^+(O)^-(CH_3)C_{16}H_{33}$
$(CH_3O)_2C_{14}H_{29}Si(CH_2)_2P^+(O)^-(C_4H_9)_2$
$(C_4H_9O)(CH_3)_2Si(CH_2)_3S^+(O)^-C_{14}H_{29}$
$(CH_3O)_2CH_3SiCH_2N^+[(C_3H_6O)_{20}H]_2C_6H_5$ $Cl^-$
$(CH_3O)_2C_2H_5Si(CH_2)_2N^+[(C_4H_8O)_6C_2H_5]_2CH_3$ $Cl^-$
$(C_2H_5O)(CH_3)_2SiCH_2P^+[(C_2H_4O)_2H](C_6H_5)_2$ $Cl^-$
$(C_2H_5O)_2C_8H_{17}Si(CH_2)_3P^+[(C_2H_4O)_4C_6H_{13}]_2C_4H_9$ $Cl^-$
$(CH_3O)_2CH_3SiCH_2P^+[(C_2H_4O)_6COCH_3]_2C_8H_{17}$ $Cl^-$
$(CH_3O)_2CH_3SiCH_2S^+[(C_3H_6O)_2H]C_{14}H_{29}$ $Cl^-$
$(C_2H_5O)(C_2H_5)_2Si(CH_2)_3S^+[(C_2H_4O)_5CH_3]C_8H_{17}$ $Br^-$
$(C_2H_5O)_2C_{10}H_{21}SiCH_2N^+[(C_2H_4O)_2COC_2H_5](C_4H_9)_2$ $Cl^-$
$(CH_3O)_2C_4H_9Si(CH_2)_2S^+[(C_2H_4O)_2COCH_3]C_{12}H_{25}$ $Br^-$

Compounds of Formulas I and II when $R_4$ is an alkyl, aryl, aryalkyl group or oxygen are disclosed in British Patents 686,068 and 882,053 and U.S. Pat. Nos. 2,955,127, 3,557,178, 3,730,701, and 3,817,739. Compounds of Formulas I and II when $R_4$ is a carboxy-substituted alkyl group or $(C_xH_{2x}O)_mZ$ are disclosed in commonly assigned copending patent application "Organosilane Compounds" by Heckert and Watt U.S. Ser. No. 570,532 filed April 22, 1975. (The disclosure of this application is herein incorporated by reference.)

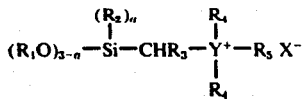
III.

wherein $R_1$ is a $C_{1-4}$ alkyl group, a is 0 to 2, $R_2$ is a $C_{2-18}$ alkyl group, $R_3$ is a $C_{1-18}$ alkyl group, $R_4$ is a $C_{1-12}$ alkyl, aryl or arylalkyl group, a carboxy-substituted $C_{1-4}$ alkyl group, $(C_xH_{2x}O)_mZ$ where $x$ is 2–4, $m$ is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

The compounds of Formula III when $a$ is 0 and $R_4$ is an alkyl, aryl or arylalkyl group are prepared by the following route:

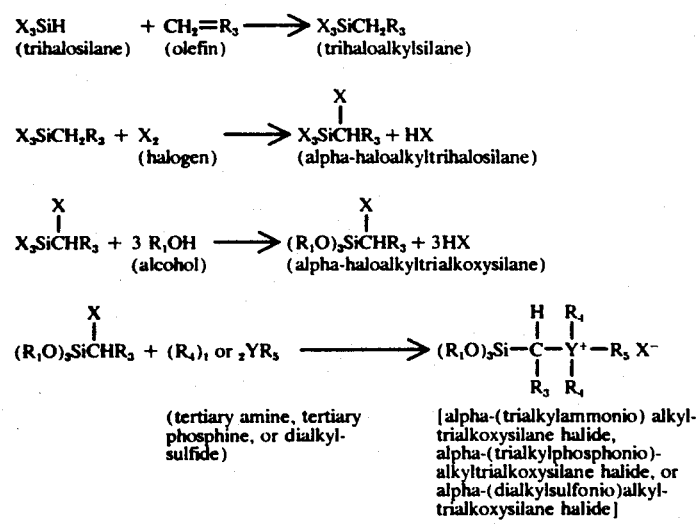

The trihalosilane is reacted with an olefin at 100° C. for 4 to 10 hours under a pressure of 50 to 300 psi. in the presence of a chloroplatinic acid or platinum catalyst to produce the trihaloalkylsilane. This reaction is reported by F. P. Mackay, O. W. Steward and P. G. Campbell in "Journal of the American Chemical Society, 79, 2764 (1957) and J. L. Speier, J. A. Webster and S. W. Barnes in Journal of the American Chemical Society, 79, 974 (1957). The trihaloalkylsilane is then halogenated in a known manner by treating it with halogen in the presence of light (such as that provided by ordinary tungsten or fluorescent lamps). Preferably, halogenation is carried out to only partial completion and a distillation is performed to recycle unreacted alkylsilane. The remaining reactions are the same as those described above in connection with the preparation of the compounds of Formula I.

When $a$ is 1 or 2, the preparation of the compounds is essentially the same except for the use of an alkyl substituted silane as the starting reactant.

When $R_4$ is a carboxy-substituted $C_{1-4}$ alkyl group, oxygen or $(C_xH_{2x}O)_mZ$ where $x$ is 2–4, $m$ is 1–20, and Z is hydrogen, a $C_{1-18}$ alkyl group, or a $C_{1-4}$ acyl group, an appropriate amine, phosphine, or sulfide is used in the reaction step as discussed above for the preparation of similarly substituted compounds of Formula I.

The compounds that follow are illustrative of compounds of Formula III.

$(C_2H_5O)_3SiCH(C_8H_{17})N^+(CH_3)_2C_{12}H_{25}$ Cl⁻
$(CH_3O)_3SiCH(C_{18}H_{37})N^+(C_2H_4COOH)_2CH_3$ Cl⁻
$(C_3H_7O)_2CH_3SiCH(C_{12}H_{25})N^+(C_2H_4OH)(CH_3)_2$ Cl⁻
$(C_4H_9O)_3SiCH(C_3H_7)N^+[(C_2H_4O)_{10}H]_2C_6H_{13}$ Br⁻
$(CH_3O)_3SiCH(C_{10}H_{21})N^+[(C_2H_4O)_2C_4H_9](CH_3)C_6H_5$ Br⁻
$(CH_3O)_3SiCH(CH_3)N^+[(C_2H_4O)_3COC_2H_5](C_2H_5)_2$ Br⁻
$(C_2H_5O)_2CH_3SiCH(C_8H_{17})N^+(O)^-(CH_3)_2$
$(CH_3O)_3SiCH(C_8H_{17})P^+(CH_3)_3$ Cl⁻
$(CH_3O)_2CH_3SiCH(CH_3)P^+(C_3H_6COOH)_2C_{14}H_{28}C_6H_5$ Cl⁻

$(C_2H_5O)_3SiCH(C_{10}H_{21})P^+(C_2H_4OH)C_4H_9$ Cl⁻
$(CH_3O)_3SiCH(C_3H_7)P^+(O)^-(CH_3)C_{12}H_{25}$
$(CH_3O)_3SiCH(C_8H_{17})P^+[(C_2H_4O)_6H]_2CH_3$ Cl⁻
$(C_2H_5O)_3SiCH(C_6H_{13})P^+[(C_3H_6O)_2C_{18}H_{37}](CH_3)_2$ Cl⁻
$(CH_3O)_3SiCH(CH_3)S^+(CH_3)C_{16}H_{33}$ Br⁻
$(C_2H_5O)_2CH_3SiCH(C_{12}H_{25})S^+(C_2H_4COOH)CH_3$ Cl⁻
$(CH_3O)_2C_{16}H_{33}SiCH(C_2H_5)S^+(C_2H_4OH)C_2H_5$ Cl⁻
$(CH_3O)_3SiCH(C_{10}H_{21})S^+(O)^-C_5H_{11}$
$(C_2H_5O)_3SiCH(C_4H_9)S^+[(C_3H_6O)_{10}H]C_6H_5$ Cl⁻
$(C_2H_5O)_3SiCH(CH_3)S^+[(C_2H_4O)_{20}C_2H_5]CH_3$ Br⁻

Commonly assigned copending patent application "Organosilane Compounds" by Heckert and Watt U.S. Ser. No. 570,537 filed Apr. 22, 1975 discloses the preparation of these compounds. (The disclosure of this application is herein incorporated by reference).

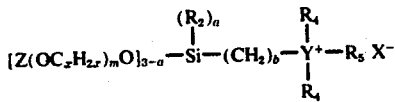

wherein Z is hydrogen, a $C_{1-18}$ alkyl group or a $C_{1-4}$ acyl group, $x$ is 2–4, $m$ is 1–20, $a$ is 0–2, $R_2$ is a $C_{1-18}$ alkyl group, $b$ is 1–3, $R_4$ is a $C_{1-12}$ alkyl, aryl or arylalkyl group, a carboxy-substituted $C_{1-4}$ alkyl group, $$(C_xH_{2x}O)_mZ$$

where $x$, $m$ and $Z$ are as defined above, or oxygen provided only one $R_4$ is oxygen, $R_5$ is a $C_{1-22}$ alkyl, aryl or arylalkyl group, X is a halide, and Y is N, S or P.

The compounds with Formula IV are prepared in substantially the same manner as those of Formula II with the exception that $R_1OH$ is $$Z(OC_xH_{2x})_mOH$$

or alternatively the compounds of Formula II are heated in the presence of $$Z(OC_xH_{2x})_mOH$$

under conditions such that $R_1OH$ is removed from the system.

Exemplary compounds of Formula IV are as follows:

[CH$_3$(OC$_2$H$_4$)O]$_3$SiCH$_2$N$^+$(CH$_3$)$_2$C$_{14}$H$_{29}$ Cl$^-$
[CH$_3$(OC$_2$H$_4$)$_5$O]$_2$CH$_3$Si(CH$_2$)$_3$N$^+$(CH$_2$COOH)$_2$C$_{10}$H$_{21}$ Cl$^-$
[H(OC$_3$H$_6$)$_3$O]$_3$SiCH$_2$N$^+$(C$_2$H$_4$OH)(CH$_3$)(C$_{12}$H$_{25}$) Cl$^-$
[H(OC$_2$H$_4$)$_{18}$O]$_3$Si(CH$_2$)$_2$N$^+$(O)$^-$(CH$_3$)C$_{18}$H$_{37}$
[CH$_3$CO(OC$_2$H$_4$)$_{10}$O]$_3$SiCH$_2$N$^+$[(C$_2$H$_4$O)$_{14}$H]$_2$C$_8$H$_{16}$C$_6$H$_5$ Cl$^-$
[C$_{16}$H$_{33}$(OC$_2$H$_4$)$_8$O]$_2$C$_6$H$_{13}$SiCH$_2$N$^+$[(C$_3$H$_6$O)CH$_3$](CH$_3$)$_2$ Br$^-$
[H(OC$_4$H$_8$)$_8$O]$_3$SiCH$_2$N$^+$[(C$_2$H$_4$O)$_4$COCH$_3$]$_3$ Cl$^-$
[C$_6$H$_{13}$(OC$_2$H$_4$)$_2$O]$_3$Si(CH$_2$)$_2$P$^+$(CH$_3$)$_2$C$_{10}$H$_{21}$ Br$^-$
[CH$_3$(OC$_3$H$_6$)$_{14}$O]$_3$SiCH$_2$P$^+$(C$_2$H$_4$COOH)(C$_6$H$_{13}$)$_2$ Cl$^-$
[C$_2$H$_5$(OC$_2$H$_4$)O]$_2$CH$_3$Si(CH$_2$)$_2$P$^-$(C$_4$H$_8$OH)(CH$_3$)C$_6$H$_5$ Cl$^-$
[CH$_3$(OC$_2$H$_4$)$_8$O]$_3$SiCH$_2$P$^+$(O)$^-$(CH$_3$)C$_8$H$_{17}$
[C$_2$H$_5$CO(OC$_2$H$_4$)$_2$O]$_3$Si(CH$_2$)$_3$P$^+$[C$_2$H$_4$O)$_8$H]$_2$C$_6$H$_{13}$ Cl$^-$
[CH$_3$(OC$_4$H$_8$)O]$_3$SiCH$_2$P$^+$[(C$_3$H$_6$O)$_2$C$_7$H$_{15}$](C$_4$H$_9$)$_2$ Br$^-$
[C$_2$H$_5$CO(OC$_2$H$_4$)O]$_3$SiCH$_2$S$^+$(CH$_3$)C$_{18}$H$_{37}$ Cl$^-$
[H(OC$_2$H$_4$)$_4$O]$_3$Si(CH$_2$)$_2$S$^+$(C$_2$H$_4$COOH)C$_{12}$H$_{25}$ Br$^-$
[CH$_3$(OC$_2$H$_4$)$_{20}$O]$_3$Si(CH$_2$)$_3$S$^+$(C$_3$H$_6$OH)C$_{16}$H$_{33}$ Br$^-$
[H(OC$_3$H$_6$)$_{12}$O]$_3$Si(CH$_2$)$_2$S$^+$(O)$^-$C$_5$H$_{11}$
[C$_{12}$H$_{25}$(OC$_2$H$_4$)$_4$O]$_3$SiCH$_2$S$^+$[(C$_2$H$_4$O)$_{20}$H]CH$_3$ Br$^-$
[H(OC$_2$H$_4$)$_{12}$O]$_3$Si(CH$_2$)$_3$S$^+$[(C$_2$H$_4$O)C$_{14}$H$_{29}$]C$_6$H$_4$CH$_3$ Cl$^-$

Commonly assigned copending patent application "Organosilane Compounds" by Heckert and Watt discloses the preparation of these compounds. (The disclosure of this application is herein incorporated by reference.)

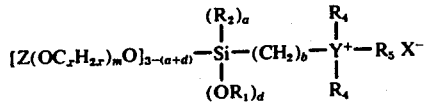

wherein Z is hydrogen, a $C_{1-18}$ alkyl group or a $C_{1-4}$ acyl group, $x$ is 2–4, $m$ is 1–20, $R_2$ is a $C_{1-18}$ alkyl group, $R_1$ is a $C_{1-4}$ alkyl group, $a$ is 0 or 1, $d$ is 1 or 2 provided $a+d$ does not exceed 2, $b$ is 1–3, $R_4$ is a $C_{1-12}$ alkyl, aryl or arylalkyl group, a carboxy-substituted $C_{1-4}$ alkyl group, $$(C_xH_{2x}O)_mZ$$

where $x$, $m$ and $Z$ are as defined above, or oxygen provided only one $R_4$ is oxygen, $R_5$ is a $C_{1-22}$ alkyl, aryl or aryl alkyl group, X is halide, and Y is N, S or P.

The compounds of Formula V are formed in substantially the same manner as those of Formula II except that a mixture of $R_1OH$ and $$Z(OC_xH_{2x})_mOH$$

in the desired ratio is used in place of $R_1OH$ or, alternatively, the compounds of Formula II are heated with less than $3-a$ equivalents of $$Z(OC_xH_{2x})_mOH$$

under conditions such that $R_1OH$ is removed from the system.

Examples of illustrative compounds follow:

[H(OC$_2$H$_4$)$_5$O](CH$_3$)(C$_2$H$_5$O)SiCH$_2$N$^+$(CH$_3$)$_2$C$_{12}$H$_{25}$ Cl$^-$
[C$_{12}$H$_{25}$(OC$_2$H$_4$)$_3$O](CH$_3$O)$_2$Si(CH$_2$)$_3$N$^+$(C$_2$H$_5$)$_2$C$_6$H$_5$ Cl$^-$
[H(OC$_4$H$_8$)$_6$O](C$_2$H$_5$O)$_2$Si(CH$_2$)$_3$N$^+$[(C$_2$H$_4$O)$_{10}$H]$_2$C$_{18}$H$_{37}$ Br$^-$
[CH$_3$CO(OC$_2$H$_4$)$_3$O]$_2$(C$_2$H$_5$O)Si(CH$_2$)$_2$N$^+$[(C$_2$H$_4$O)C$_2$H$_5$](C$_6$H$_5$CH$_3$)$_2$ Cl$^-$
[H(OC$_2$H$_4$)$_{12}$O](C$_4$H$_8$O)$_2$SiCH$_2$N$^+$[(C$_2$H$_4$O)$_4$COCH$_3$]$_2$C$_{14}$H$_{29}$ Cl$^-$
[C$_{16}$H$_{33}$(OC$_2$H$_4$)$_3$O](C$_2$H$_5$)(CH$_3$O)SiCH$_2$N$^+$(O)$^-$(CH$_3$)C$_6$H$_{13}$
[H(OC$_3$H$_6$)$_{12}$O](C$_2$H$_5$O)$_2$SiCH$_2$N$^+$(C$_2$H$_5$COOH)(CH$_3$)C$_{10}$H$_{21}$ Cl$^-$
[C$_2$H$_5$(OC$_2$H$_4$)$_{14}$O]$_2$(C$_4$H$_9$O)Si(CH$_2$)$_3$N$^+$(C$_4$H$_8$OH)(CH$_3$)C$_{14}$H$_{29}$ Cl$^-$
[H(OC$_2$H$_4$)$_{16}$O]$_2$(CH$_3$O)SiCH$_2$P$^+$(CH$_3$)$_2$C$_6$H$_4$C$_2$H$_5$ Cl$^-$
[C$_3$H$_7$(OC$_2$H$_4$)$_6$O](C$_2$H$_5$)(CH$_3$O)SiCH$_2$P$^+$[(C$_2$H$_4$O)$_8$H]$_2$C$_8$H$_{17}$ Br$^-$
[CH$_3$CO(OC$_2$H$_4$)$_2$O]$_2$(CH$_3$O)Si(CH$_2$)$_2$P$^+$[(C$_3$H$_6$O)$_3$C$_2$H$_5$](C$_4$H$_9$)$_2$ Cl$^-$
[H(OC$_4$H$_8$)$_2$O](C$_{12}$H$_{25}$)(CH$_3$O)SiCH$_2$P$^+$(O)$^-$(CH$_3$)C$_6$H$_5$ 2
[C$_{14}$H$_{29}$(OC$_2$H$_4$)$_6$O](CH$_3$O)$_2$SiCH$_2$P$^+$(C$_3$H$_6$COOH)$_2$CH$_3$ Cl$^-$
[H(OC$_2$H$_4$)$_8$O]$_2$(C$_4$H$_9$O)SiCH$_2$P$^+$(C$_3$H$_6$OH)$_2$C$_2$H$_5$ Br$^-$
[H(OC$_2$H$_4$)$_{10}$O]$_2$(C$_3$H$_7$O)SiCH$_2$S$^+$(CH$_3$)C$_6$H$_{12}$C$_6$H$_5$ Cl$^-$
[H(OC$_4$H$_8$)$_2$O]$_2$(CH$_3$O)Si(CH$_2$)$_3$S$^+$[(C$_2$H$_4$O)$_4$H]CH$_3$ Br$^-$
[C$_{12}$H$_{25}$(OC$_2$H$_4$)$_6$O](CH$_3$)(CH$_3$O)SiCH$_2$S$^+$[(C$_3$H$_6$O)$_8$CH$_3$]C$_3$H$_7$ Cl$^-$
[CH$_3$CO(OC$_2$H$_4$)$_3$O](C$_2$H$_5$O)$_2$Si(CH$_2$)$_2$S$^+$(C$_2$H$_4$OH)C$_{12}$H$_{25}$ Cl$^-$
[CH$_3$(OC$_3$H$_6$)$_{12}$O](CH$_3$O)$_2$SiCH$_2$S$^+$(C$_3$H$_6$COOH)CH$_2$C$_6$H$_5$ Br$^-$
[H(C$_2$H$_4$O)$_6$O](C$_{12}$H$_{25}$)(CH$_3$O)SiCH$_2$S$^+$(O)$^-$C$_{14}$H$_{29}$

Commonly assigned copending patent application "Organosilane Compounds" by Heckert and Watt U.S. Ser. No. 570,539, filed Apr. 22, 1975 discloses the preparation of these compounds. (The disclosure of this application is herein incorporated by reference.)

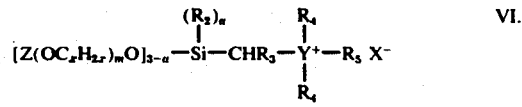

wherein Z is hydrogen, a $C_{1-18}$ alkyl group or a $C_{1-14}$ acyl group, x is 2–4, m is 1–20, a is 0–2, $R_2$ is a $C_{1-18}$ alkyl group, $R_3$ is a $C_{1-18}$ alkyl group, $R_4$ is a $C_{1-12}$ alkyl, aryl or arylalkyl group, a carboxy-substituted $C_{1-4}$ alkyl group, $$(C_xH_{2x}O)_mZ$$

where x is 2–4, m is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide and Y is N, S or P.

The compounds of Formula VI are formed in the same manner as those of Formula III with the exception that $$Z(OC_xH_{2x})_mOH$$

is used in place of $$R_1OH$$

during the alcoholysis of the halo-silane. Alternatively, preparation may be effected by the heating of compounds of Formula III with $$Z(OC_xH_{2x})_mOH$$

under conditions such that all of the $$R_1OH$$

is removed from the system.

The following compounds illustrate the compounds of Formula VI.

[CH$_3$(OC$_2$H$_4$)$_3$O]$_3$SiCH(CH$_3$)N$^+$(CH$_3$)$_2$C$_{18}$H$_{37}$ Cl$^-$
[C$_2$H$_5$(OC$_2$H$_4$)O]$_2$CH$_3$SiCH(C$_2$H$_5$)N$^+$(C$_2$H$_4$OH)$_2$C$_{14}$H$_{29}$ Cl$^-$
[H(OC$_4$H$_8$)$_8$O]$_3$SiCH(C$_4$H$_9$)N$^+$(C$_2$H$_4$COOH)(C$_4$H$_9$)CH$_2$C$_6$H$_5$ Cl$^-$
[CH$_3$CO(OC$_2$H$_4$)$_2$O]$_3$SiCH(C$_2$H$_5$)N$^+$(O)$^-$(CH$_3$)C$_{10}$H$_{21}$
[H(OC$_3$H$_6$)$_6$O]$_3$SiCH(C$_{12}$H$_{25}$)N$^+$[(C$_2$H$_4$O)$_{10}$H]$_2$CH$_3$ Br$^-$
[C$_{12}$H$_{25}$(OC$_2$H$_4$)O]$_3$SiCH(C$_3$H$_7$)N$^+$[(C$_4$H$_8$O)$_3$C$_5$H$_{10}$](C$_2$H$_5$)$_2$ Cl$^-$
[C$_{10}$H$_{21}$(OC$_2$H$_4$)$_4$O]$_3$SiCH(C$_2$H$_5$)N$^+$[(C$_2$H$_4$O)$_6$COCH$_3$]$_2$CH$_3$ Cl$^-$
[H(OC$_2$H$_4$)$_{16}$O]$_3$SiCH(C$_8$H$_{17}$)P$^+$(C$_2$H$_5$)$_2$C$_6$H$_4$C$_4$H$_9$ Cl$^-$
[CH$_3$(OC$_2$H$_4$)$_{16}$O]$_2$C$_{12}$H$_{25}$SiCH(CH$_3$)P$^+$(C$_2$H$_4$COOH)$_2$C$_{10}$H$_{21}$ Cl$^-$
[C$_2$H$_5$OC(OC$_2$H$_4$)$_5$O]$_3$SiCH(CH$_3$)P$^+$(C$_2$H$_4$OH)(CH$_3$)C$_{12}$H$_{25}$ Cl$^-$
[H(OC$_2$H$_4$)$_2$O]$_3$SiCH(C$_{10}$H$_{25}$)P$^+$(O)$^-$(CH$_3$)C$_{16}$H$_{33}$
[H(OC$_2$H$_4$)$_2$O]$_3$SiCH(C$_8$H$_{17}$)P$^+$[(C$_2$H$_4$O)$_6$H]$_2$C$_4$H$_9$ Br$^-$
[CH$_3$(OC$_4$H$_8$)$_2$O]$_3$SiCH(CH$_3$)P$^+$[(C$_2$H$_4$O)C$_8$H$_{17}$](CH$_3$)$_2$ Cl$^-$
[C$_{10}$H$_{21}$(OC$_2$H$_4$)$_2$O]$_3$SiCH(C$_6$H$_{13}$)S$^+$(CH$_3$)C$_{10}$H$_{21}$ Cl$^-$
[H(OC$_2$H$_4$)$_{14}$O]$_2$CH$_3$SiCH(C$_8$H$_{17}$)S$^+$(C$_2$H$_4$COOH)C$_{18}$H$_{37}$ Cl$^-$
[H(OC$_3$H$_6$)$_4$O]$_3$SiCH(C$_{14}$H$_{29}$)S$^+$(C$_4$H$_8$OH)C$_6$H$_5$ Cl$^-$
[CH$_3$CO(OC$_2$H$_4$)$_3$O]$_3$SiCH(C$_2$H$_5$)S$^+$(O)$^-$C$_{18}$H$_{37}$
[C$_{12}$H$_{25}$(OC$_2$H$_4$)O]$_3$SiCH(C$_3$H$_7$)S$^+$[(C$_3$H$_6$O)H]C$_6$H$_{13}$ Cl$^-$
[H(OC$_4$H$_8$)$_4$O]$_2$CH$_3$SiCH(C$_4$H$_9$)S$^+$[C$_2$H$_4$O)$_8$C$_3$H$_7$]CH$_3$ Br$^-$

Commonly assigned copending patent application "Organosilane Compounds" by Heckert and Watt U.S. Ser. No. 570,537 filed Apr. 22, 1975 discloses the preparation of these compounds. (The disclosure of this application is herein incorporated by reference.)

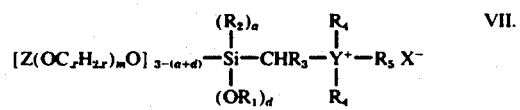

wherein Z is hydrogen, a $C_{1-18}$ alkyl group or a $C_{1-4}$ acyl group, x is 2–4, m is 1–20, $R_2$ is a $C_{1-8}$ alkyl group, $R_1$ is a $C_{1-4}$ alkyl group, a is 0 or 1, d is 1 or 2 provided a+d does not exceed 2, $R_3$ is a $C_{1-18}$ alkyl group, $R_4$ is a $C_{1-12}$ alkyl, aryl or arylalkyl group, a carboxy-substituted $C_{1-4}$ alkyl group, $(C_xH_{2x}O)_mZ$ where a, m and Z are as defined above, or oxygen provided only one $R_4$ is oxygen, $R_5$ is a $C_{1-22}$ alkyl, aryl or arylalkyl group, X is halide and Y is N, S or P.

Compounds having Formula VII are prepared in substantially the same manner as those of Formula III except that a mixture of $$R_1OH$$

and $$Z(OC_xH_{2x})_mOH$$

in the desired ratio is used in place of $R_1OH$. Alternatively, the compounds of Formula III are heated together with less than 3–a equivalents of $$Z(OC_xH_{2x})_mOH$$

under conditions such that $R_1OH$ is removed from the system.

The following compounds are illustrative of the compounds of Formula VII:

[H(OC$_2$H$_6$)$_6$O](C$_2$H$_5$O)$_2$SiCHC$_{12}$H$_{25}$N$^+$[(C$_2$H$_4$O)$_{10}$H]$_2$C$_{18}$H$_{37}$ Br$^-$
[CH$_3$CO(OC$_2$H$_4$)$_3$O]$_2$(C$_2$H$_5$O)SiCHCH$_3$N$^+$[(C$_2$H$_4$O)C$_2$H$_5$]$_2$C$_6$H$_5$CH$_3$ Cl$^-$
[H(OC$_2$H$_4$)$_{12}$O](C$_4$H$_9$O)$_2$SiCHC$_2$H$_5$N$^+$[(C$_2$H$_4$O)$_4$COCH$_3$]$_2$C$_{14}$H$_{29}$ Cl$^-$
[C$_{16}$H$_{33}$(OC$_2$H$_4$)$_3$O](C$_2$H$_5$)(CH$_3$O)SiCHCH$_3$N$^+$(O)$^-$(CH$_3$)C$_6$H$_{13}$
[C$_2$H$_5$(OC$_2$H$_4$)$_{14}$O]$_2$(C$_4$H$_9$O)SiCHC$_6$H$_{13}$N$^+$(C$_6$H$_{12}$OH)(CH$_3$)C$_{14}$H$_{29}$ Cl$^-$
[H(OC$_2$H$_4$)$_{16}$O]$_2$(CH$_3$O)SiCHC$_4$H$_9$P$^+$(CH$_3$)$_2$C$_{18}$H$_{37}$ Cl$^-$
[CH$_3$CO(OC$_2$H$_4$)$_2$O]$_2$(CH$_3$O)SiCHC$_{16}$H$_{33}$P$^+$[(C$_3$H$_7$O)$_3$C$_2$H$_5$](C$_4$H$_9$)$_2$ Cl$^-$
[C$_{14}$H$_{29}$(OC$_2$H$_4$)$_6$O](CH$_3$O)$_2$SiCHCH$_3$P$^+$(C$_3$H$_6$COOH)$_2$CH$_3$ Cl$^-$
[H(OC$_2$H$_4$)$_{10}$O]$_2$(C$_3$H$_7$O)SiCHC$_5$H$_{11}$S$^+$(CH$_3$)C$_{12}$H$_{25}$ Cl$^-$
[H(OC$_4$H$_8$)$_2$O]$_2$(CH$_3$O)SiCHC$_8$H$_{17}$S$^+$CH$_3$C$_6$H$_5$ Br$^-$

Commonly assigned copending patent application "Organosilane Compounds" by Heckert and Watt U.S. Ser. No. 570,537 filed Apr. 22, 1975 the preparation of the compounds. (The disclosure of this application is herein incorporated by reference.)

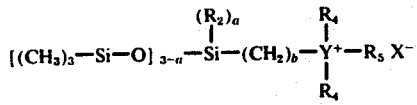

wherein *a* is 0–2, $R_2$ is $C_{1-18}$ alkyl group, *b* is 1–3, $R_4$ is a $C_{1-12}$ alkyl, aryl or arylalkyl group, a carboxy-substituted $C_{1-4}$ alkyl group, $$(C_xH_{2x}O)_mZ$$

where *x* is 2–4, *m* is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

When 2 is 0, a tris(trimethylsiloxy) silane is used as the starting reactant. Commercially available trihalosilanes and trimethylsilanes are used to produce the starting reactant. Subsequent reaction steps and conditions as discussed in the preparation of compounds of Formula I are used to produce the desired compound of Formula VI.

When *a* is 1 or 2, a corresponding compound of Formula II is reacted with trimethylchlorosilane at an elevated temperature, e.g., 50° C. to 200° C. to obtain the desired organosilane.

Examples of compounds of Formula VIII are:

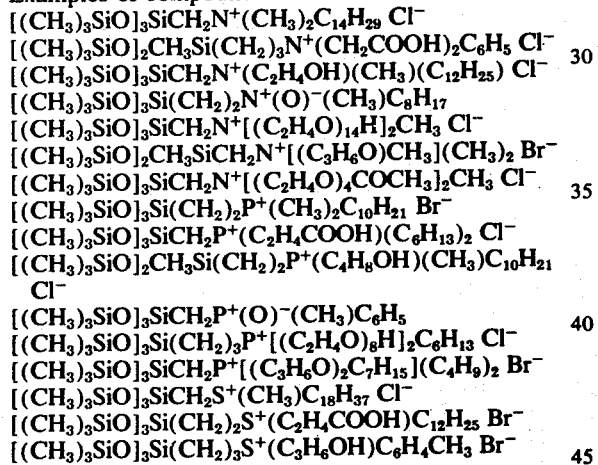

Commonly assigned copending patent application "Organosilane Compounds " by Heckert and Watt U.S. Ser. No. 570,538, filed Apr. 22, 1975 discloses the preparation of the compounds when $R_4$ is a carboxy-substituted alkyl group or $$(C_xH_{2x}O)_mZ$$

(The disclosure of this application is herein incorporated by reference.) U.S. Pat. Nos. 2,955,127, 3,624,120 and 3,658,867 discloses the compounds when $R_4$ is alkyl, aryl, arylalkyl or oxygen.

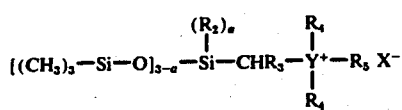

wherein *a* is 0–2, $R_2$ is a $C_{1-18}$ alkyl group, $R_3$ is a $C_{1-12}$ alkyl, aryl or arylalkyl group, a carboxy-substituted $C_{1-4}$ alkyl group, $$(C_xH_{2x}O)_mZ$$

where *x* is 2-4, *m* is 1-20, and Z is hydrogen, a $C_{1-18}$ alkyl group or a $C_{1-14}$ acyl group, or oxygen provided only one $R_4$ is oxygen, $R_5$ is a $C_{1-22}$ alkyl, aryl or arylalkyl group, X is halide and Y is N, S or P.

When *a* is 0, the compounds of Formula IX are prepared following the description given for the preparation of the compounds of Formula III with the exception that a tris(trimethylsiloxy)silane is used as the starting reactant. When *a* is 1 or 2, a corresponding compound of Formula III is reacted with a trimethylchlorosilane at about 50° C. to 200° C. to produce the desired organosilane.

Illustrative compounds of Formula IX follow:

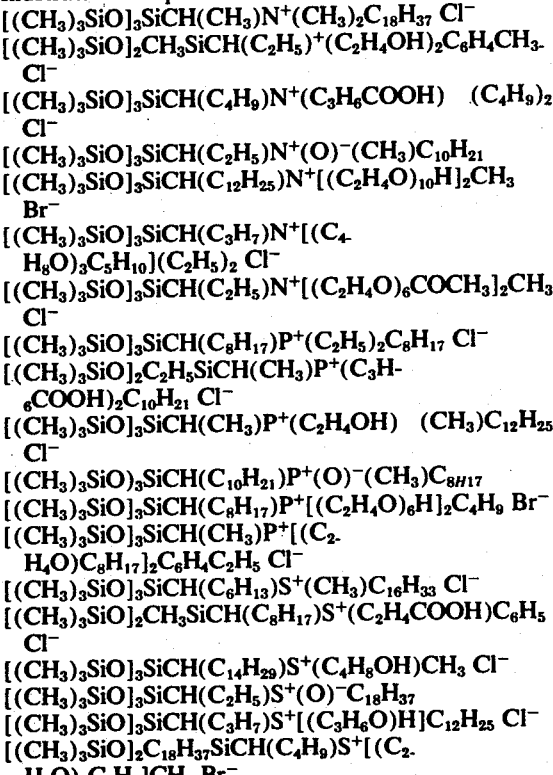

Commonly assigned copending patent application "Organosilane Compounds" by Heckert and Watt U.S. Ser. No. 570,537 filed Apr. 22, 1975 discloses the preparation of these compounds. (The disclosure of this application is herein incorporated by reference.)

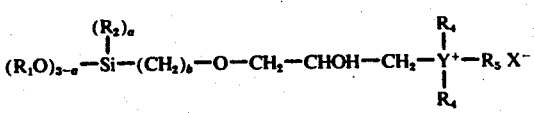

wherein $R_1$ is a $C_{1-4}$ alkyl group, *a* is 0-2, $R_2$ is a $C_{1-18}$ alkyl group, *b* is 1-3, $R_4$ is a $C_{1-12}$ alkyl, aryl or arylalkyl group, a carboxy-substituted $C_{1-4}$ alkyl group, $$(C_xH_{2x}O)_mZ$$

where *x* is 2-4, m is 1-20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide and Y is N, S or P.

The compounds of Formula X are prepared by initially reacting (when a is 0 and b is 3) trihalosilane with an alcohol ($R_1$OH) at 0° C. to 50° C. for 1 to 10 hours to produce a trialkoxysilane. This silane is then reacted with an allylglycidylether

(CH₂=CHCH₂OCH₂CHCH₂)

in the presence of 0:01% to 0.1% chloroplatinic acid or platinum at 100° C. for 2 to 10 hours. The resultant product

[(R₁O)₃Si—(CH₂)₃OCH₂CHCH₂]

is reacted with a tertiary amine, tertiary phosphine, or dialkylsulfide in the presence of an acid in an inert solvent at 60° C. to 100° C. for 1 to 10 hours to produce the compound of Formula X.

When $a$ is 1 or 2, the preparation of the compounds is essentially the same except for the use of an alkyl substituted silane as the starting reactant.

When b is 2 in formula X, a trihalovinylsilane of formula $$X_3SiCH=CH_2$$

(which is commercially available) is reacted with hydrogen bromide in the presence of peroxide or light to produce a beta-haloethyltrihalosilane. This compound is reacted with an alcohol, an allylglycidylether, and finally with an appropriate amine, phosphine, or sulfide in the manner discussed above for the preparation of the compounds of Formula X when b is 3.

When $b$ is 1 in Formula X, the starting reactant is a commercially available trihalomethylsilane of formula $$X_3SiCH_3$$

This silane is reacted with chlorine or, preferably a half mole of bromine and a half mole of chlorine in the presence of light (such as provided by an ordinary tungsten or fluorescent lamp). The resultant alpha-halomethyltrihalosilane is reacted with an alcohol, an allylglycidylether, and finally an appropriate amine, phosphine, or sulfide in the manner discussed above with the compounds of Formula X when b is 3.

The following compounds illustrate the compounds of Formula X.

$(CH_3O)_3Si(CH_2)_3OCH_2CHOHCH_2N^+(CH_3)_2C_{16}H_{33}$ Cl⁻
$(CH_3O)_2C_{12}H_{25}SiCH_2OCH_2CHOHCH_2N^+(C_3H_6COOH)(C_4H_9)C_8H_{17}$ Cl⁻
$(C_2H_5O)_3Si(CH_2)_2OCH_2CHOHCH_2N^+(C_2H_4OH)_2C_6H_5$ Br⁻
$(CH_3O)_3Si(CH_2)_3OCH_2CHOHCH_2N^+(O)^-(CH_3)C_8H_{17}$
$(CH_3O)_3SiCH_2OCH_2CHOHCH_2N^+[(C_2H_4O)H]_2C_{14}H_{29}$ Br⁻
$(CH_3O)_2C_2H_5SiCH_2OCH_2CHOHCH_2N^+[(C_3H_6O)_{12}C_2H_5](CH_3)_2$ Cl⁻
$(C_4H_9O)_3SiCH_2OCH_2CHOHCH_2N^+[(C_2H_4O)_3COCH_3]_2CH_3$ Br⁻
$(CH_3O)_3SiCH_2OCH_2CHOHCH_2P^+(C_4H_9)_2CH_2C_6H_5$ Br⁻
$(C_4H_9O)_3SiCH_2OCH_2CHOHCH_2P^+(C_2H_4COOH)_2C_8H_{17}$ Cl⁻
$(CH_3O)_3Si(CH_2)_2OCH_2CHOHCH_2P^+(C_2H_4OH)(C_2H_5)C_{10}H_{21}$ Cl⁻
$(CH_3O)_3SiCH_2OCH_2CHOHCH_2P^+(O)^-(CH_3)C_{18}H_{37}$
$(CH_3O)_3SiCH_2OCH_2CHOHCH_2P^+[C_3H_6O)_{18}H]_2CH_3$ Br⁻
$(C_2H_5O)(CH_3)_2SiCH_2OCH_2CHOHCH_2P^+[(C_2H_4O)CH_3]_2C_6H_{13}$
$(CH_3O)_3SiCH_2OCH_2CHOHCH_2S^+(CH_3)C_6H_4CH_3$ Cl⁻
$(CH_3O)_2C_{16}H_{37}SiCH_2OCH_2CHOHCH_2S^+(C_2H_4COOH)C_8H_{17}$ Cl⁻
$(CH_3O)_3Si(CH_2)_2OCH_2CHOHCH_2S^+(C_2H_4OH)C_6H_{13}$ Cl⁻
$(C_2H_5O)_3SiCH_2OCH_2CHOHCH_2S^+(O)^-C_{10}H_{21}$
$(CH_3O)_3SiCH_2OCH_2CHOHCH_2S^+[(C_2H_4O)_{12}H]CH_3$ Br⁻
$(C_2H_5O)_3SiCH_2OCH_2CHOHCH_2S^-[(C_2H_4O)_2C_8H_{17}]C_2H_5$ Br⁻

Commonly assigned copending patent application "Organosilane Compounds" by Heckert and Watt U.S. Ser. No. 570,531 filed Apr. 22, 1975 discloses the preparation of these compounds. (The disclosure of this application is herein incorporated by reference.)

$$[Z(O C_xH_{2x})_mO]_{3-a}\text{—}SSi\text{—}(CH_2)_b\text{—}O\text{—}CH_2\text{—}CHOH\text{—}CH_2\text{—}\overset{R_4}{\underset{R_4}{Y^+}}\text{—}R_5\ X^- \quad XI.$$

with $(R_2)_a$ on the Si.

wherein Z is hydrogen, a $C_{1-18}$ alkyl group or a $C_{1-4}$ acyl group, $x$ is 2–4, $m$ is 1–20, $a$ is 0–2, $R_2$ is a $C_{1-18}$ alkyl group, $b$ is 1–3, $R_4$ is a $C_{1-12}$ alkyl, aryl, or arylalkyl group, a carboxy-substituted $C_{1-4}$ alkyl group, $$(C_xH_{2x}O)_mZ$$

where $x$ is 2–4, $m$ is 1–20, and Z is hydrogen, a $C_{1-18}$ alkyl group or a $C_{1-4}$ acyl grop, or oxygen provided only one $R_4$ is oxygen, $R_5$ is a $C_{1-22}$ alkyl, aryl or arylalkyl group, X is a halide, and Y is N, S or P.

Compounds of Formula XI are prepared in a manner identical with that of Formula X except that R₁OH is replaced by $$HO(C_xH_{2x}O)_mZ.$$

The following compounds are exemplary of Formula XI compounds.

$[H(OC_2H_4)_{20}O]_3SiCH_2OCH_2CHOHCH_2N^+(CH_3)_2C_{10}H_{21}$ Cl⁻
$[CH_3(OC_3H_6)_{10}O]_2CH_3SiCH_2OCH_2CHOHCH_2N^+(C_2H_4COOH)(C_4H_9)_2$ Cl⁻
$[C_2H_5(OC_2H_4)_2O]_3Si(CH_2)_3OCH_2CHOHCH_2N^+(C_2H_4OH)_2(C_8H_{17})$ Cl⁻
$[C_8H_{17}(OC_2H_4)O]_3SiCH_2OCH_2CHOHCH_2N^+(O)^-(C_4H_9)C_6H_5$
$[CH_3CO(OC_2H_4)_6O]_3Si(CH_2)_2OCH_2CHOHCH_2N^+[(C_2H_4O)_{10}H]_2CH_3$ Cl⁻
$[H(OC_3H_6)_8O]_2C_{16}H_{33}SiCH_2OCH_2CHOHCH_2N^+[(C_2H_4O)_8C_4H_9](CH_3)_2$ Br⁻
$[C_2H_5(OC_2H_4)_4O]_3SiCH_2OCH_2CHOHCH_2N^+[(C_2H_4O)_2COCH_3]_2CH_3$ Br⁻
$[C_{18}H_{39}(OC_2H_4)_3O]_3SiCH_2OCH_2CHOHCH_2P^+(C_2H_5)_2C_{14}H_{29}$ Cl⁻
$[H(OC_3H_6)_8]_3Si(CH_2)_3OCH_2CHOHCH_2P^+(C_3H_6COOH)_2C_6H_{13}$ Cl⁻

[C₈H₁₇(OC₂H₄)₂O]₂CH₃SiCH₂OCH₂CHOHCH₂P⁺(C₂H₄OH)(CH₃)C₈H₁₇ Cl⁻

[CH₃(OC₃H₆)₃O]₃Si(CH₂)₃OCH₂CHOHCH₂P⁺(O)⁻(CH₃)C₁₀H₂₁

[C₂H₅(OH₄C₂)₁₂O]₃Si(CH₂)₂OCH₂CHOHCH₂P⁺[(C₂H₄O)₂H]₂C₆H₄CH₃ Br⁻

[CH₃CO(OC₂H₄)₈O]₃SiCH₂OCH₂CHOHCH₂P⁺[(C₃H₆O)₈C₂H₅](C₄H₉)₂ Cl⁻

[H(OC₂H₄)₄O]₃SiCH₂OCH₂CHOHCH₂S⁺(CH₃)C₁₈H₃₇ Cl⁻

[C₁₆H₃₃(OC₂H₄)₆O]₂C₁₂H₂₅SiCH₂OCH₂CHOHCH₂S⁺(C₃H₆COOH)C₁₀H₂₁ Cl⁻

[CH₃(OC₄H₈)₄O]₃SiCH₂OCH₂CHOHCH₂S⁺(C₄H₈OH)C₈H₁₇ Br⁻

[H(OC₂H₄)₁₄O]₃Si(CH)₂OCH₂CHOHCH₂S⁺(O)⁻C₁₂H₁₄C₆H₅

[C₉H₁₉(OC₂H₄)O]₃SiCH₂OCH₂CHOHCH₂S⁺[(C₂H₄O)₆H]C₆H₁₃ Cl⁻

[C₂H₅CO(OC₂H₄)₂O]₃SiCH₂OCH₂CHOHCH₂S⁺[(C₄H₈O)₁₂CH₃]C₈H₁₇ Cl⁻

Commonly assigned copending patent application "Organosilane Compounds" by Heckert and Watt (P&G Case 2215) filed of even date discloses the preparation of these compounds. (The disclosure of this application is herein incorporated by reference.)

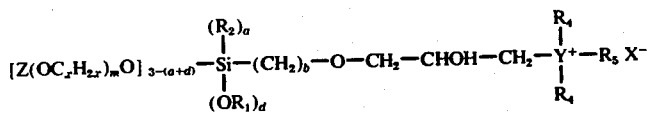

XII.

wherein Z is hydrogen, a C₁₋₁₈ alkyl group or a C₁₋₄ acyl group, x is 2–4, m is 1–20, R₂ is a C₁₋₁₈ alkyl group, R₁ is a C₁₋₄ alkyl group, a is 0 or 1, d is 1 or 2 provided a+d does not exceed 2, b is 1–3, R₄ is a C₁₋₂ alkyl, aryl or arylalkyl group, a carboxy-substituted C₁₋₄ alkyl group, $(C_xH_{2x}O)_mZ$ where x, m and Z are as defined above, or oxygen provided only one R₄ is oxygen, R₅ is a C₁₋₂₂ alkyl, aryl or arylalkyl group, X is halide, and Y is N, S or P.

These compounds are prepared in a manner similar to that described for the compounds of Example XI except that only a part of the R₁OH is replaced by $HO(C_xH_{2x}O)_mZ$.

The following compounds are examples of compounds having the Formula XII.

[H(OC₂H₄)₁₂O](CH₃O)₂SiCH₂OCH₂CHOHCH₂N⁺(CH₃)₂C₁₈H₃₇ Cl⁻

[H(OC₃H₆O)₃O](C₂H₅O)(CH₃)Si(CH₂)₂OCH₂CHOHCH₂N⁺(CH₂COOH)(CH₄H₉)₂ Cl⁻

[C₁₂H₂₅(OC₂H₄)₉O](C₂H₅O)₂SiCH₂OCH₂CHOHCH₂N⁺(C₄H₈OH)₂CH₃ Cl⁻

[CH₃(OC₄H₈)₂O]₂(C₄H₉O)Si(CH₂)₃OCH₂CHOHCH₂N⁺(O)⁻(CH₃) C₁₆H₃₃

[CH₃CO(OC₂H₄)₆O]₂(CH₃O)SiCH₂OCH₂CHOHCH₂N⁺[(C₂H₄O)₈H]₂CH₃ Br⁻

[H(OC₂H₄)₁₈O](C₂H₅O)(C₁₆H₃₃)SiCH₂OCH₂CHOHCH₂N⁺[(C₂H₄O)C₁₂H₂₅](CH₃)₂ Cl⁻

[H(OC₂H₄)₈O](C₂H₅O)₂SiCH₂OCH₂CHOHCH₂P⁺(CH₃)₂C₆H₅ Cl⁻

[CH₃(OC₂H₄)₆O](C₁₂H₂₅)(CH₃O)SiCH₂OCH₂CHOHCH₂P⁺[(C₂H₄O)₆OCH₃]₂(CH₃) Cl⁻

[CH₃CO(OC₃H₆)₄O]₂(CH₃O)Si(CH₂)₃OCH₂CHOHCH₂P⁺(C₄H₈OH)₂CH₃ Cl⁻

[H(OC₄H₈)₂O](CH₃O)(CH₃)SiCH₂OCH₂CHOHCH₂S⁺[(C₂H₄O)₃H]C₂H₅ Cl⁻

[C₁₂H₂₅(OC₂H₄)O](C₄H₉O)₂Si(CH₂)₂OCH₂CHOHCH₂S⁺(C₃H₆COOH)CH₃ Br⁻

[C₂H₅CO(OC₂H₄)₁₀O]₂(C₂H₅O)SiCH₂OCH₂CHOHCH₂S⁺(O)⁻C₁₂H₂₅

Commonly assigned copending patent application "Organosilane Compounds" by Heckert and Watt (P&G Case 2215) filed of even date discloses the preparation of these compounds. (The disclosure of this application is herein incorporated by reference.)

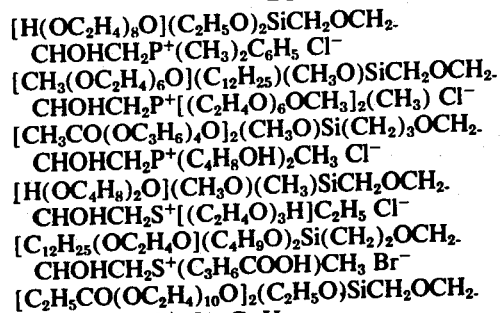

XIII.

wherein a is 0–2, R₂ is a C₁₋₁₈ alkyl group, b is 1–3, R₄ is a C₁₋₁₂ alkyl, aryl or arylalkyl group, a carboxy-substituted C₁₋₄ group, $(C_xH_{2x}O)_mZ$ where x is 2–4, m is 1–20, and Z is hydrogen, a C₁₋₁₈ alkyl group or a C₁₋₄ acyl group, or oxygen provided only one R₄ is oxygen, R₅ is a C₁₋₂₂ alkyl, aryl or arylalkyl group, X is halide, and Y is N, S or P.

Tris(trimethylsiloxy)silanes, which are prepared from commercially available trimethylhalosilanes and trihalosilanes, are used as the starting reactants when a is 0. Subsequent reaction steps and conditions as discussed with the preparation of compounds of Formula X are used to produce the desired compound of Formula XIII.

When a is 1 or 2, a compound of Formula X is reacted with trimethylchlorosilane at an elevated temperature, e.g. 50° C. to 200° C. to obtain the desired organosilane.

The following compounds are illustrative of the compounds of Formula XIII.

[(CH₃)₃SiO]₃SiCH₂OCH₂CHOHCH₂N⁺(CH₃)₂C₁₀H₂₁ Cl⁻

[(CH₃)₃SiO]₂CH₃SiCH₂OCH₂CHOHCH₂N⁺(C₂H₄COOH)(C₄H₉)₂ Cl⁻

[(CH₃)₃SiO]₃Si(CH₂)₃OCH₂CHOHCH₂N⁺(C₂H₄OH)₂C₈H₁₇ Cl⁻

[(CH₃)₃SiO]₃SiCH₂OCH₂CHOHCH₂N⁺(O)⁻(C₂H₅)C₆H₄C₂H₅

[(CH₃)₃SiO]₃Si(CH₂)₂OCH₂CHOHCH₂N⁺[(C₂H₄O)₁₀H]₂CH₃ Cl⁻

[(CH₃)₃SiO]₂C₂H₅SiCH₂OCH₂CHOHCH₂N⁺[(C₂H₄O)₈C₄H₉](CH₃)₂ Br⁻

[(CH₃)₃SiO]₃SiCH₂OCH₂CHOHCH₂N⁺[(C₃H₆O)₂COCH₃]₂CH₃ Br⁻

[(CH₃)₃SiO]₃SiCH₂OCH₂CHOHCH₂P⁺(C₂H₅)₂C₁₄H₂₉ Cl⁻

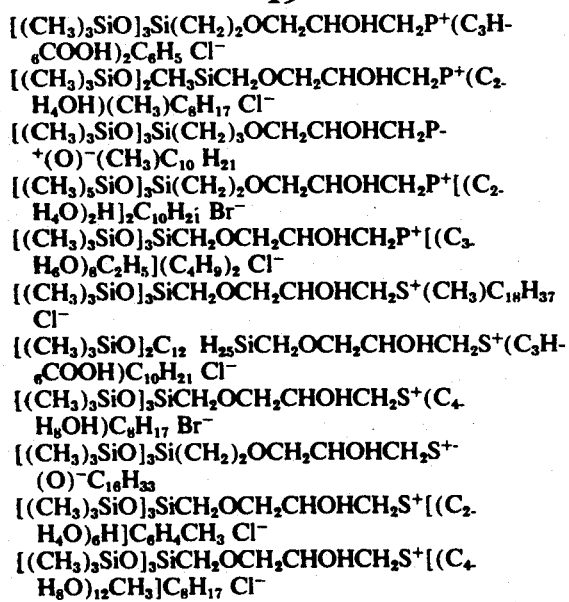

U.S. Pat. No. 3,389,160 discloses compounds of Formula XIII when $R_4$ is an alkyl, aryl, or arylalkyl group. Commonly assigned patent application, "Organosilane Compounds" by Heckert and Watt, U.S. Ser. No. 570,338 filed Apr. 22, 1975 discloses the preparation of the other compounds. (The disclosure of this application is herein incorporated by reference).

Siloxane oligomers of the above organosilanes are also useful in the present invention. Such oligomers are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably 2 to 20. A higher degree of polymerization adversely affects the ability of the compound to bond itself to the hard surface and is for this reason avoided. Examples of siloxane oligomers having varying degrees of polymerization are readily visualized from the above examples of organosilane monomers.

The organosilane represents from 2% to 50%, preferably 5% to 25% of the carrier granule.

The water-soluble or water-dispersible nonionic material of this invention is normally solid, i.e. melts or liquefies between the temperature of 35° C. and 95° C., preferably from 40° C. to 65° C. and is preferably non-hydroscopic. A wide variety of nonionic materials fitting the above criteria are useful in the context of the present invention. Specific examples of materials suitable for use in this invention are:

(1) The condensation products of one mole of a saturated or unsaturated, straight or branched chain carboxylic acid having from about 10 to about 18 carbon atoms with from about 20 to about 50 moles of ethylene oxide, which liquefy between the temperatures of about 35° C. and about 95° C. and are solid at temperatures below about 35° C. The acid moiety can consist of mixtures of acids in the above-delineated carbon atoms range or it can consist of an acid having a specific number of carbon atoms within this range. The condensation product of one mole of coconut fatty acid having the approximate carbon chain length distribution of 2% $C_{10}$, 66% $C_{12}$, 23% $C_{14}$, and 9% $C_{16}$ with 35 moles of ethylene oxide is a specific example of a nonionic containing a mixture of different chain length fatty acid moieties. Other specific examples of nonionics of this type are: the condensation products of one mole of palmitic acid with 40 moles of ethylene oxide; the condensation product of one mole of myristic acid with 35 moles of ethylene oxide; the condensation product of one mole of oleic acid with 45 moles of ethylene oxide; and the condensation product of one mole of stearic acid with 30 moles of ethylene oxide.

2. The condensation products of one mole of a saturated or unsaturated straight or branched chain alcohol having from about 10 to about 24 carbon atoms with from about 10 to about 50 moles of ethylene oxide which liquefy between the temperatures of about 35° C. and 95° C. and are solid at temperatures below about 35° C. The alcohol moiety can consist of alcohols in the above-delineated carbon atom range or it can consist of an alochol having a specific number of carbon atoms within this range. The condensation product of one mole of coconut alcohol having the approximate chain length distribution of 2% $C_{10}$, 66% $C_{12}$, 23% $C_{14}$, and 9% $C_{16}$ with 45 moles of ethylene oxide ($CNAE_{45}$) is a specific and highly preferred example of a nonionic containing a mixture of different chain length alcohol moieties. Other specific examples of nonionics of this type are the condensation products of one mole of tallow alcohol with 20 moles of ethylene oxide; the condensation products of one mole of lauryl alcohol with 35 moles of ethylene oxide; the condensation products of one mole of myristyl alcohol with 30 moles of ethylene oxide; and the condensation products of one mole of oleyl alcohol with 40 moles of ethylene oxide.

3. Two specific examples of nonionic surface active agents suitable for use in this invention and not specifically classified herein are polyoxyethylene glyceride esters having a hydrophilic-lipophilic balance (HLB) of 18.1 and polyoxyethylene lanolin derivatives having an HLB of 17.0. Both nonionics are manufactured by Atlas Chemical Industries, Inc.; the trade name of the former is G-1300 and the trade name of the latter is G-1795. The HLB number is an indication of the percentage weight of the hydrophilic portion of the nonionic molecule divided by 5.

4. Amides which have a melting point between about 35° C. and 95° C. are also suitable for use in this invention. Specific examples are propyl amide, N-methyl amides having an acyl chain length of from about 10 to about 15 carbon atoms, pentyl anilide and anilides having a carbon chain length of from about 7 to about 12 carbon atoms, oleamide, amides of ricinoleic acid, N-isobutyl amides of pelargonic acid, capric acid, undecanoic acid and lauric acid, N-(2-hydroxyethyl) amides having a carbon chain length of from about 6 to about 10 carbon atoms, N-cyclopentyllauramide and N-cyclopentylstearamide.

5. The polyethylene glycols having a molecular weight of from about 4000 to about 30,000, preferably 4000 to 20,000. For example, Dow Chemical Company manufactures these nonionics in molecular weights of 20,000, 9500, 4500, 3400 and 1450. All of these nonionics are waxlike, solids which melt between 35° C. and 95° C.

6. The condensation products of one mole of alkyl phenol wherein the alkyl chain contains from about 8 to about 18 carbon atoms with from about 25 to about 50 moles of ethylene oxide. Specific examples of these nonionics are the condensation products of one mole of decyl phenol with 40 moles of ethylene oxide; the condensation products of one mole of dodecyl phenol with 35 moles of ethylene oxide; the condensation products of one one of tetradecyl phenol with 35 moles of ethylene oxide; the condensation products of one mole of hexadecyl phenol with 30 moles of ethylene oxide.

7. Fatty acid containing from about 12 to about 30 carbon atoms which melt between 35° C. and 95° C. Specific examples of these nonionics are lauric acid, myristic acid, palmitic acid, stearic acid, tallow acid or mixtures of tallow acid and coconut acid, arachidic acid, behenic acid and ligoceric acid. Fatty acids are nonionic when utilized as a conglutinating agent. When the finished granules are utilized in alkaline solutions, however, the fatty acids are saponified to soap, an anionic surface active agent. Fatty acids having from 12 to 18 carbon atoms are preferred for use herein.

8. Fatty alcohols containing from about 16 to about 30 carbon atoms which melt between 35° C. and 95° C. Specific examples of these nonionics are 1-hexadecanol, 1-octadecanol, 1-eicosanol, 1-heneicosanol, 3-docosanol, 1-tetracosanol and 1-octacosanol.

Normally solid water-soluble or -dispersible nonionic materials other than those listed above can also be used in this invention provided they are compatible with the organosilane. The nonionic material represents from 3% to 70%, preferably 10% to 45% of the carrier granule.

In one aspect of the invention, the inert core material is given a first coating of the organosilane and thereafter given a second or outer coating of the normally solid nonionic material. It should be understood that the organosilane coating can actually penetrate into the inner core, though it substantially forms a true coating. According to this aspect of the invention, the inert core material is agitated (e.g. in a fluidized bed) and sprayed with a solution of the organosilane in a solvent. Satisfactory solvents include lower alcohols, i.e. $C_{1-4}$ alcohols and methyl ethyl ketone. The lesser the concentration of organosilane in the solvent, the greater will be its penetration into the inner core. Generally, 5% to 95% of organosilane in solvent is satisfactory. The solvent is thereafter evaporated away. The water-soluble or water-dispersible normally solid nonionic material is normally melted and sprayed onto the organosilane-coated inner core. Alternatively, the normally solid material is dissolved in a solvent and applied to the organosilane-coated inner core.

In another aspect of the invention, the organosilane and normally solid nonionic material are mixed together prior to their being applied to the inner core material. A slurry of melted normally solid nonionic material and the organosilane or a solvent mixture of the materials are applied to the inner core material. Detergent compositions intended for use on metallic or vitreous surfaces where a soil release benefit is desired utilize the hereindescribed carrier granules. Such compositions contain water-soluble organic, nonionic, anionic, zwitterionic, ampholytic detergents or mixtures thereof. U.S. Pat. No. 3,579,454, issued May 18, 1971 to Everett J. Collier, Col. 11, line 49 to Col. 13, line 64, discloses detergents of the above class and is herein incorporated by reference. Such detergent compositions also contain water either in a free or hydrated form and contain an electrolyte and/or have an alkaline pH, i.e. a pH above 7.0.

If an anionic detergent is used, the organosilane preferably has a total of no more than 20 carbon atoms in the $R_2$, $R_3$, $R_4$ (when $R_4$ is an alkyl, aryl, arylalkyl group or a carboxy-substituted alkyl group) and $R_5$ groups. Additionally, $R_2$, $R_3$ and $R_5$ contain 1 to 12 carbon atoms and, when Z is an alkyl group, it contains 1 to 3 carbon atoms. Also $R_1$ is either the alkyl group or

$$Z(OC_xH_{2x})_m.$$

The granules of this invention are added to a detergent composition at a level such that the ratio of organosilane to detergent is from 1:1 to 1:10,000, preferably 1:1 to 1:500, most preferably 1:3 to 1:60.

A preferred detergent composition which contains the carrier granules are automatic dishwasher detergent compositions. Such preferred compositions contain from 0.01% to 5%, preferably 0.1% to 2%, organosilane, (exclusive of the remainder of the carrier granule), from 0.1% to 15%, preferably 1% to 5% of a water-soluble nonionic organic detergent, from 5% to 60%, preferably 30% to 50% of a water-soluble organic or inorganic alkaline builder salt; and the balance inert filler salts. Suitable alkaline builder salts include sodium tripolyphosphate, sodium citrate, sodium carbonate, and sodium nitrilotriacetate. Suitable inert filler salts include sodium sulfate and chloride.

An alkali metal silicate having a $SiO:M_2O$ ratio of from 3.6:1 to 1:2 (where M = alkali metal, preferably sodium) at a level of from 7% to 35%, preferably 10% to 20% may optionally be added to the automatic dishwashing composition. A chlorine bleach capable of giving the composition from 0.2% to 10%, preferably 0.5% to 5% available chlorine content is also optionally included. Chlorinated trisodium phosphate and sodium dichlorocyanurate are preferred chlorine bleaches.

An alkali metal base, e.g. sodium or potassium hydroxide is added at a level of from 10% to 40%, preferably 10% to 30% when the composition is used for commercial dishwashing machines.

The carrier granules of this invention also find use in a detergent-free commercial automatic dishwashing machine composition. Such compositions consist essentially of from 0.01% to 5%, preferably 0.1% to 2% of the organosilane, from 5% to 60%, preferably 30% to 50% of the alkaline builder salt, from 10% to 40%, preferably 10% to 30% of the alkali metal base and the balance inert filler salts. Suitable alkaline builder salts, alkali metal bases and filler salts have been discussed above. Alkali metal silicates and chlorine bleaches may optionally be included at the levels stated immediately above.

Carrier granules of this invention also find use in a detergent-free toilet bowl cleaner. Such compositions consist essentially of from 0.01% to 5%, preferably 0.5% to 2% of the organosilane; from 50% to 90%, preferably 75% to 85% sodium bisulfate; and the balance inert filler salts.

The above stated amounts of organosilane is exclusive of the core material and nonionic material which is associated with the organosilane in the carrier granule.

The organosilanes of this invention, when not a part of a carrier granule, lose some of their efficacy upon storage when included in this composition. This is evident by the formation of water-insoluble excessively polymerized organosilanes. A significant improvement is realized when the organosilane forms a part of the hereindescribed carrier granule.

When a detergent composition containing the carrier granules of this invention is added to water, the nonionic material either solubilizes or disperses thereby freeing the organosilane. As previously discussed the organosilane is able to bond to a metallic or vitreous surface and impart soil release properties thereto. It is theorized that the positively charged atom in the organosilane molecule is attracted to the negatively charged hard surface and is responsible for the organosilane deposition occurring from the dilute conditions in which the compositions of this invention are used.

EXAMPLE I

A carrier granule is produced by forming a fluidized bed of sucrose. Onto the sucrose is sprayed a mixture of 80% melted polyethylene glycol (PEG) having a molecular weight of 4000 and 20% of an organosilane having the formula $(C_2H_5O)_3SiCH_2N^+(CH_3)_2C_{12}H_{25}\ Cl^-$ The coated carrier granules which are collected comprise an inner core of sucrose representing 38% of the granule and an outer coating of organosilane and PEG representing 12% and 50% of the granule, respectively.

Example of other suitable carrier granules follow:

EXAMPLE II

| | |
|---|---|
| Sucrose | 68.0% |
| PEG (MW = 4000) | 5.5% |
| $(CH_3O)_2C_2H_5Si(CH_2)_3P^+(CH_3)_2C_8H_{17}\ Cl^-$ | 26.5% |

The sucrose represents the inner core while the PEG and organosilane form a single coating on the inner core.

EXAMPLE III

| | |
|---|---|
| PEG (M.W. = 6000) | 68.0% |
| $(C_2H_5O)_3SiCH_2N^+\ (CH_3)_2(C_2H_4O)_4C_2H_5\ Cl^-$ | 6.0% |
| PEG (M.W. = 4000) | 26.0% |

The PEG (6000) represents the inner core. A 80% solution of the organosilane in ethanol is sprayed onto the inner core. After the ethanol has been evaporated, melted PEG 4000 is sprayed onto the organosilane-coated PEG 6000.

EXAMPLE IV

| | |
|---|---|
| Sodium sulfate | 50.0% |
| $(CH_3O)_3Si(CH_2)_3N^+(CH_3)_2(C_2H_4COOH)C_{10}H_{21}\ Cl^-$ | 30.0% |
| Stearic acid | 20.0% |

The stearic acid and organosilane form a single coating surrounding the sulfate.

EXAMPLE V

| | |
|---|---|
| Sodium bicarbonate | 65% |
| $(CH_3SiO)_3SiCH_2N^+(CH_3)_2C_8H_{17}\ Br^-$ | 10% |
| Palmitic acid ethoxylated with 40 moles of ethylene oxide | 25% |

The organosilane forms a coating on the sodium bicarbonate with the ethoxylated palmitic acid forming a separate outer layer.

EXAMPLE VI

| | |
|---|---|
| Sodium sulfate | 75% |
| $(CH_3O)_3SiCH(C_{14}H_{29})N^+(CH_3)_2C_2H_5\ Cl^-$ | 5% |
| Propylamide | 20% |

The propylamide and organosilane form a homogeneous coating on the sodium sulfate.

EXAMPLE VII

| | |
|---|---|
| Sucrose | 68% |
| $(C_2H_5O)_3Si(CH_3)_2N^+\ (O)^-(CH_3)C_{18}H_{37}$ | 6% |
| 1-octadecanol | 26% |

The organosilane forms an inner coating with the 1-octadecanol forming an outer coating.

EXAMPLE VIII

| | |
|---|---|
| PEG 6000 (flakes) | 70% |
| $(CH_3O)_3Si(CH_2)_2N^+(C_2H_5)(C_2H_4OH)(C_8H_{17})\ Cl^-$ | 10% |
| Tallow fatty acid | 20% |

The tallow fatty acid is an outer coating on the organosilane coated PEG 6000.

EXAMPLE IX

| | |
|---|---|
| Sodium sulfate | 65% |
| $(CH_3O)_3SiCH_2OCH_2CHOHCH_2N^+(CH_3)_2C_5H_{11}\ Cl^-$ | 5% |
| PEG (9500) | 30% |

The PEG and organosilane form a homogeneous coating on the sodium sulfate.

EXAMPLE X

| | |
|---|---|
| Sodium sulfate | 50% |
| $(C_2H_5O)_3SiCH_2S^+(CH_3)C_{16}H_{33}\ Cl^-$ | 10% |
| PEG 4000 | 40% |

The sodium sulfate is the inner core of the carrier granule with the organosilane forming a coating thereon and the PEG 4000 forming an outer coating.

EXAMPLE XI

An automatic dishwashing detergent composition of the following composition is formulated:

| | |
|---|---|
| Sodium tripolyphosphate | 41.1% |
| Chlorinate trisodium phosphate | 8.8% |
| Sodium silicate (SiO$_2$:Na$_2$O = 2.4) | 12.5% |
| Tallow alcohol ethoxylated with 9 moles of ethylene oxide | 2.4% |
| Water | 24.8% |
| Carrier granule | 8.5% |
| Miscellaneous (perfume, dyes, etc.) | Balance |

The carrier granule is the granule of Example I.

A soil release benefit is imparted to cooking utensils and tableware washed with the above composition as evidenced by the easier cleaning encountered in subsequent washings compared to the same composition not containing the organosilane.

The above composition has greater storage stability than a similar composition wherein the organosilane is not a part of a carrier granule.

Substantially the same results are obtained when the carrier granules of Examples II – X are substituted for for the above carrier granule (keeping the organosilane content constant).

When the organosilanes that immediately follow are substituted for the organosilane used in making the carrier granule of Example I and the resultant carrier granules are used in the detergent composition of Example XI, substantially the same soil release benefits are noticed even after prolonged periods of storage.

$C_2H_5O)_3SiCH_2N^+(CH_3)_2C_{12}H_{25}$ $Cl^-$
$C_2H_5O)_3SiCH_2P^+(CH_3)_2C_{12}H_{25}$ $Cl^-$
$(C_2H_5O)_3Si(CH_2)_2N^+(CH_3)_2C_{12}H_{25}$ $Cl^-$
$(C_2H_5O)_3Si(CH_2)_3N^+(CH_3)_2C_{12}H_{25}$ $Br^-$
$(C_2H_5O)_3SiCH_2N^+(CH_3)_2C_6H_{13}$ $Cl^-$
$(CH_3O)_3SiCH_2N^+(CH_3)_2CH_2C_6H_5$ $Cl^-$
$(C_2H_5O)_3SiCH_2N^+(CH_3)_2C_{18}H_{37}$ $Cl^-$
$(C_2H_5O)_3SiCH_2S^+(CH_3)C_{18}H_{37}$ $Cl^-$
$C_4H_8O)_3SiCH_2N^+(CH_3)_2C_{12}H_{24}C_6H_5$ $Cl^-$
$CH_3O)_3SiCH_2N^+[(C_3H_6O)_3C_2H_5]_2C_8H_{17}$ $Cl^-$
$(CH_3O)_2CH_3SiCH(C_{18}H_{37})N^+(CH_3)_3$ $Br^-$
$(C_2H_5O)_3Si(CH_2)_3N^+(C_2H_5)$ $[(C_4H_9)_8H]C_4H_9$ $Cl^-$
$(C_2H_5O)_3SiCH_2N^+(C_3H_7COOH)_2C_8H_{17}$ $Cl^-$
$(C_2H_5O)_3SiCH_2N^+[(C_2H_4O)_4COCH_3]_2C_{18}H_{37}$ $Cl^-$
$[(CH_3)_3SiO]_3SiCH_2N^+(CH_3)_2C_{12}H_{25}$ $Br^-$
$(C_2H_5O)_3SiCH(C_{12}H_{25})N^+(C_2H_5)_3$ $Cl^-$
$(C_2H_5O)_3SiCH(C_{12}H_{25})P^+(C_2H_5)_3$ $Cl^-$
$(CH_3O)_2CH_3SiCH(C_{18}H_{37})S^+(CH_3)_2$ $Br^-$
$(C_2H_5O)_3SiCH_2N^+(O)^-(CH_3)C_{14}H_{29}$
$(C_2H_5O)_3SiCH_2S^+(O)^-C_{14}H_{29}$
$(CH_3O)_3Si(CH_2)_3N^+(CH_3)_2C_6H_4C_3H_7$ $Cl^-$
$(CH_3O)_3SiCH_2N^+(C_2H_4OH)(CH_3)C_{12}H_{25}$ $Cl^-$
$(CH_3O)_3Si(CH_2)_3OCH_2CHOHCH_2N^+(CH_3)_2C_8H_{17}$ $Cl^-$
$(C_2H_5O)_2C_4H_9SiCH_2N^+(CH_3)_2C_{12}H_{25}$ $Cl^-$
$[H(OC_2H_4)_{18}O]]_3SiCH_2N^+(C_2H_5)_2C_{18}H_{37}$ $Cl^-$
$[CH_3(OC_2H_4)_{12}O]_2CH_3SiCH_2N^+(CH_3)_2C_{12}H_{25}$ $Br^-$
$[CH_3CO(OC_2H_4)_4]_3Si(CH_2)_3N^+(CH_3)_2C_{10}H_{21}$ $Cl^-$
$[H(OC_2H_4)_n](CH_3O)_2SiCH_2N^+(CH_3)_2C_{12}H_{25}$ $Cl^-$
$[CH_3(OC_2H_4)_6O]_3SiCH(C_{12}H_{25})N^+(CH_3)_3$ $Br^-$
$[H(OC_2H_4)_2O]_2(CH_3O)SiCH(C_8H_{17})N^+(CH_3)_2C_6H_{13}$ $Cl^-$
$[(CH_3)_3SiO]_3SiCH(C_{16}H_{33})N^+(CH_3)_2C_4H_9$ $Cl^-$
$[H(OC_2H_4)_4O]_3SiCH_2OCH_2\cdot$
$CHOHCH_2N^+(CH_3)_2C_{12}H_{25}$ $Cl^-$
$[CH_3(OC_2H_4)_8O]_2(CH_3O)SiCH_2OCH_2\cdot$
$CHOHCH_2N^+(C_4H_9)_3$ $Cl^-$
$[(CH_3)_3SiO]_3SiCH_2OCH_2\cdot$
$CHOHCH_2N^+(CH_3)_2C_{14}H_{29}$ $Br^-$
$[(CH_3)_3SiO]_3SiCH_2OCH_2CHOHCH_2P^+(CH_3)_2C_{14}H_{29}$ $Br^-$
Siloxane dimer of $(C_2H_5O)_3SiCH_2N^+(CH_3)_2C_{12}H_{25}$ $Cl^-$
Siloxane dimer of $(C_2H_5O)_2(CH_3)SiCH_2N^+(CH_3)_2C_{16}H_{33}$ $Cl^-$
Siloxane trimer of $(CH_3O)_3Si(CH_2)_3P^+(CH_3)_2C_{12}H_{25}$ $Cl^-$
Siloxane dimer of $(CH_3O)_3SiCH_2S^+(CH_3)C_{12}H_{25}$ $Cl^-$

We claim:

1. A carrier granule containing an organosilane compound which comprises an inner core of an inert, organic or inorganic material whose surface has thereon an organosilane and a water-soluble or water-dispersible, normally solid, nonionic material consisting essentially of:

a. from 25% to 95% of a water-soluble or water-dispersible inert organic or inorganic granular material which is inert to the organosilane, non-hygroscopic, non-electrolytic and non-alkaline and serves as the inner core;

b. from 2% to 50% of an organosilane having the formula

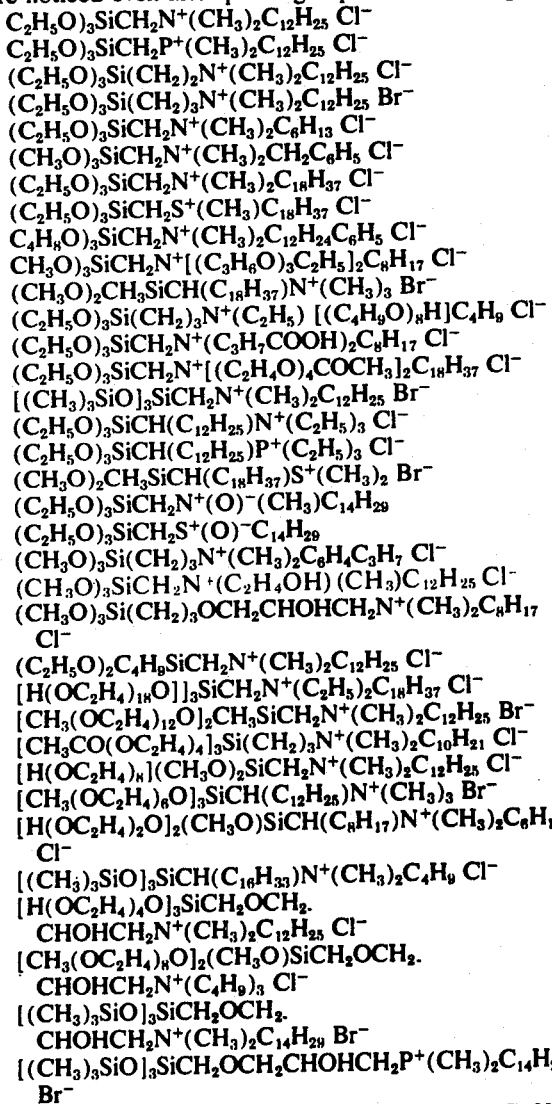

or is a siloxane oligomer thereof wherein $R_1$ is an alkyl group containing 1 to 4 carbon atoms, $$(CH_3)_3 \text{ Si or } Z(C_xH_{2x})_m$$

where $x$ is 2 to 4, $m$ is 1 to 20, and Z is hydrogen, an alkyl group containing 1 to 18 carbons or an acyl group containing 1 to 4 carbon atoms; $R_2$ is an alkyl group containing 1 to 18 carbon atoms; $a$ is 0 to 2; $R_3$ is hydrogen or an alkyl group containing 1 to 18 carbon atoms; $b$ is 1 to 3, $c$ is 0 or 1; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and Z are as defined above, or oxygen provided only one $R_4$ is oxygen and further provided that there is no $X^-$ when $R_4$ is oxygen; $R_5$ is an alkyl, aryl or arylalkyl group containing 1 to 22 carbon atoms; X is bromide or chloride; and Y is nitrogen, sulfur or phosphorus; and c. from 3% to 70% of a water soluble or water-dispersible, normally solid nonionic material which melts or liquifies between the temperatures of 35° C and 95° C and wherein the organosilane and nonionic material are on the surface of the inner core.

2. The carrier granule of claim 1 wherein the organosilane has the formula

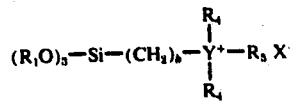

or is a siloxane oligomer thereof wherein $R_1$ is an alkyl group containing 1 to 4 carbon atoms; $b$ is 1 to 3; $R_4$ is a alkyl, aryl or arylalkyl group containing 1 to 12 carbon atoms, a carboxy-substituted alkyl group containing 1 to 4 carbon atoms, $$(C_xH_{2x}O)_mZ$$

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 4 to 22 carbon atoms; X is bromide or chloride; and Y is nitrogen, sulfur or phosphorus.

3. The carrier granule of claim 1 wherein the organosilane has the formula

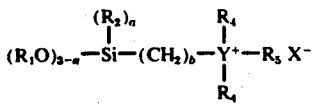

or is a siloxane oligomer thereof wherein $R_1$ is an alkyl group containing 1 to 4 carbon atoms; $R_2$ is an alkyl group containing 1 to 18 carbon atoms; $a$ is 1 or 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

4. The carrier granule or claim 1 wherein the organosilane has the formula

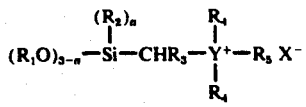

or is a siloxane oligomer thereof wherein $R_1$ is an alkyl group containing 1 to 4 carbon atoms; $R_2$ is an alkyl group containing 1 to 18 carbon atoms; $a$ is 0 to 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms.

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided than when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

5. The carrier granule of claim 1 wherein the organosilane has the formula

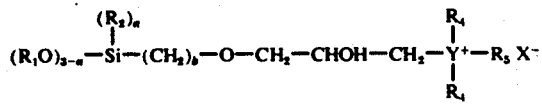

or is a siloxane oligomer thereof wherein $R_1$ is an alkyl group containing 1 to 4 carbon atoms; $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

6. The carrier granule of claim 1 wherein $b$ is 1.

7. The carrier granule of claim 1 wherein the inert, inner core material represents from 50% to 75% of the composition, the organosilane represents from 5% to 25% of the composition and the nonionic material represents from 10% to 45% of the granule.

8. The carrier granule of claim 1 wherein the organosilane is coated onto the inner core with the nonionic material forming an outer coating.

9. The carrier granule of claim 1 wherein the organosilane and nonionic material form a substantially homogeneous mixture which coats the inner core.

10. The carrier granule of claim 1 wherein the inner core is selected from the group consisting of flaked polyethylene glycol having a molecular weight of from 4000 to 30000, sodium sulfate, sulfite, bicarbonate, acetate and anhydrous citrate and sucrose.

11. The carrier granule of claim 1 wherein the nonionic material is a polyethyleneglycol having a molecular weight of from 4000 to 20000.

12. The carrier granule of claim 1 wherein said inert organic or inorganic granular material serving as inner core, is selected from the group consisting of flaked polyethylene glycol having a molecular weight of from 4,000 to 30,000, sodium sulfate, sodium sulfite, sodium bicarbonate, sodium acetate and anhydrous sodium citrate and sucrose and said water soluble or water dispersible, normally solid nonionic material melts or liquifies between the temperatures of 35° C and 95° C and is selected from the group consisting of (1) condensation products of 1 mole of a saturated or unsaturated, straight or branched chain carboxylic acid having from about 10 to about 18 carbon atoms with from about 20 to about 50 moles of ethylene oxide; (2) the condensation products of 1 mole of saturated or unsaturated, straight or branched chain alcohol having from about 10 to about 24 carbon atoms with from about 10 to about 50 moles of ethylene oxide; (3) polyoxyethylene glyceride esters having a hydrophilic-lipophilic balance of 18.1; (4) polyoxyethylene lanolin derivatives having a hydrophilic-lipophilic balance of 17.0; (5) amides; (6) polyethylene glycols having a molecular weight of from about 1,400 to about 30,000; (7) the condensation products of 1 mole of alkylphenol wherein the alkyl chain contains from about 8 to about 18 carbon atoms with from about 25 to about 50 moles of ethylene oxide; (8) fatty acid containing from about 12 to about 30 carbon atoms; (9) fatty alcohols containing from about 16 to about 30 carbon atoms; (10) water-soluble wax; (11) and mixtures thereof.

13. The carrier granule of claim 1 wherein said nonionic material is non-hygroscopic.

14. The carrier granule of claim 1 wherein the organosilane has the formula

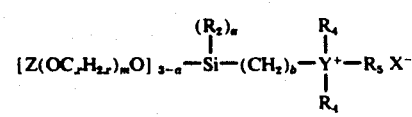

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms, $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and $Z$ are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

15. The carrier granule of claim 1 wherein the organosilane has the formula

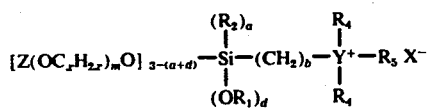

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $R_1$ is an alkyl group containing 1 to 4 carbon atoms, $a$ is 0 or 1; $d$ is 1 or 2 provided $a+d$ does not exceed 2; $b$ is 1 to 3; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and $Z$ are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

16. The carrier granule of claim 1 wherein the organosilane has the formula

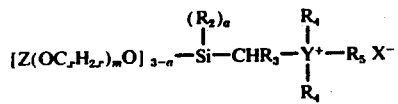

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $a$ is 0 to 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and $Z$ are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

17. The carrier granule of claim 1 wherein the organosilane has the formula

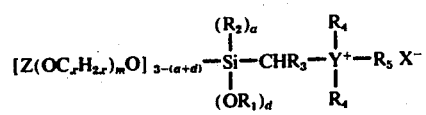

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $R_1$ is an alkyl group containing 1 to 4 carbon atoms; $a$ is 0 or 1, $d$ is 1 or 2 provided $a+d$ does not exceed 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and $Z$ are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

18. The carrier granule of claim 1 wherein the organosilane has the formula

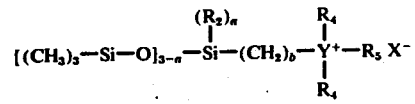

or is a siloxane oligomer thereof wherein $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

19. The carrier granule of claim 1 wherein the organosilane has the formula

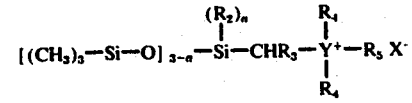

or is a siloxane oligomer thereof wherein $R_2$ is an alkyl group containing 1 to 18 carbon atoms; $a$ is 0 to 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

20. The carrier granule of claim 1 wherein the organosilane has the formula

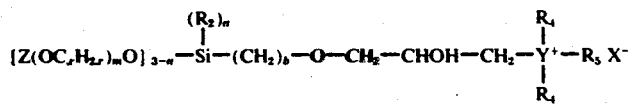

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

21. The carrier granule of claim 1 wherein the organosilane has the formula

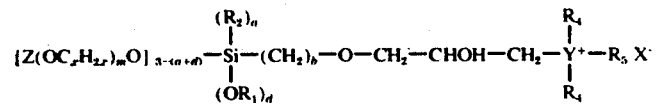

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $R_1$ is an alkyl group containing 1 to 4 carbon atoms; $a$ is 0 or 1, $d$ is 1 or 2 provided $a+d$ does not exceed 2; $b$ is 1 to 3; $R_4$ is an alkyl, aryl or arylalkyl group containing 1 to 12 carbon atoms, a carboxy-substituted alkyl group containing 1 to 4 carbon atoms,

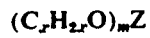

where $x$, $m$ and Z are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

22. The carrier granule of claim 1 wherein the organosilane has the formula

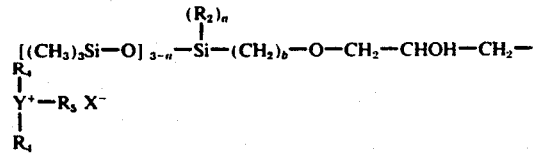

or is a siloxane oligomer thereof wherein $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

23. The granule of claim 1 in which said organosilane has the formula

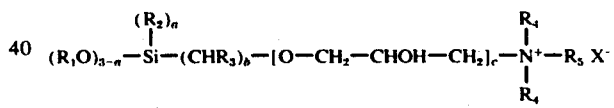

or is a siloxane oligomer thereof wherein $R_1$ is an alkyl group containing 1 to 4 carbon atoms,

where $x$ is 2 to 4, $m$ is 1 to 20, and Z is hydrogen, an alkyl group containing 1 to 18 carbons or an acyl group containing 1 to 4 carbon atoms; $R_2$ is an alkyl group containing 1 to 18 carbon atoms; $a$ is 0 to 2; $R_3$ is hydrogen or an alkyl group containing 1 to 18 carbon atoms; $b$ is 1 to 3; $c$ is 0 or 1; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen and further provided than when $R_4$ is oxygen there is no $X^-$; $R_5$ is an alkyl, aryl or arylalkyl group containing 1 to 22 carbon atoms; bromide or chloride.

* * * * *

UNITED STATES PATENT AND TRADEMARK OFFICE
CERTIFICATE OF CORRECTION

PATENT NO. : 4,013,573

DATED : March 22, 1977

INVENTOR(S) : John W. Leikhim, Edward J. Maguire, Jr., David C. Heckert, David M. Watt, Jr.

It is certified that error appears in the above-identified patent and that said Letters Patent are hereby corrected as shown below:

Column 2, line 1, "a organsilane" should be -- an organosilane --.

Column 2, line 50, "or" should be -- of --.

Column 3, line 42, "$C_{1-28}$" should be -- $C_{1-18}$ --.

Column 4, line 19, "2 to 20" should be -- 2 to 10 --.

Column 4, line 38, "59°C." should be -- 50°C. --.

Column 5, line 53,

"$(CH_3O)_3SICH_2N(C_2H_4OH)_2C_{18}H_{37}Cl^-$" should be

-- $(CH_3O)_3SICH_2N^+(C_2H_4OH)_2C_{18}H_{37}Cl^-$ --.

Column 5, line 61,

"$(C_2H_5O)_3Si(CH_2)_3N^+[(C_2H_4O(_6H]_2C_{10}H_{21}Cl^-$" should be

-- $(C_2H_5O)_3Si(CH_2)_3N^+[(C_2H_4O)_6H]_2C_{10}H_{21}Cl^-$ --.

Column 7, line 15, "$C_{2-18}$" should be -- $C_{1-18}$ --.

Column 9, line 39,

"$[H(OC_4H_8)_8O]_3SiCH_2N^+[(C_2H_4O)_4COCH_3]_3Cl^-$" should be

-- $[H(OC_4H_8)_8O]_3SiCH_2N^+[(C_2H_4O)_4COCH_3]_2CH_3\ Cl^-$ --.

UNITED STATES PATENT AND TRADEMARK OFFICE
CERTIFICATE OF CORRECTION

PATENT NO. : 4,013,573
DATED : March 22, 1977
INVENTOR(S) : John W. Leikhim et al It is certified that error appears in the above-identified patent and that said Letters Patent are hereby corrected as shown below:

Column 9, line 43,

"$[C_2H_5(OC_2H_4)O]_2CH_3Si(CH_2)_2P^-(C_4H_8OH)(CH_3)C_6H_5\ Cl^-$" should be -- $[C_2H_5(OC_2H_4)O]_2CH_3Si(CH_2)_2P^+(C_4H_8OH)(CH_3)C_6H_5\ Cl^-$ --.

Column 9, line 58, after "Watt" insert -- U.S. Serial No. 570,539, filed April 22, 1975, --.

Column 11, line 4, "$C_{1-14}$" should be -- $C_{1-4}$ --.

Column 12, line 18, "$C_{1-8}$" should be -- $C_{1-18}$ --.

Column 12, line 22, "a" should be -- x --.

Column 12, line 66, after "1975" insert -- discloses --.

Column 13, line 16, "2" should be -- a --.

Column 14, line 4, "$C_{1-14}$" should be -- $C_{1-4}$ --.

Column 14, line 50, insert -- X --.

Column 15, line 4, "0:01%" should be -- 0.01% --.

Column 16, line 19, "$(C_2H_5O)_3SiCH_2OCH_2CHOHCH_2S^-[(C_2$" should be -- $(C_2H_5O)_3SiCH_2CHOHCH_2S^+[(C_2$ --.

UNITED STATES PATENT AND TRADEMARK OFFICE
CERTIFICATE OF CORRECTION

PATENT NO. : 4,013,573
DATED : March 22, 1977
INVENTOR(S) : John W. Leikhim et al It is certified that error appears in the above-identified patent and that said Letters Patent are hereby corrected as shown below:

Column 16, line 26,

"$[Z(OC_xH_{2x})_mO]_{3-a} - SSi\overset{(R_2)_a}{\underset{|}{\phantom{S}}} -$" should be -- $[Z(OC_xH_{2x})_mO]_{3-a} - Si\overset{(R_2)_a}{\underset{|}{\phantom{S}}} -$ --.

Column 17, line 42, "$C_{1-2}$" should be -- $C_{1-12}$ --.

Column 19, line 27, "570,338" should be -- 570,538 --.

Column 25, line 16, "$C_2H_5O)_3SiCH_2N^+(CH_3)_2C_{12}H_{25}\ Cl^-$" should be -- $(C_2H_5O)_3SiCH_2N^+(CH_3)_2C_{12}H_{25}\ Cl^-$ --.

Column 25, line 17, "$C_2H_5O)_3SiCH_2P^+(CH_3)_2C_{12}H_{25}\ Cl^-$" should be -- $(C_2H_5O)_3SiCH_2P^+(CH_3)_2C_{12}H_{25}\ Cl^-$ --.

Column 25, line 24, "$C_4H_8O)_3SiCH_2N^+(CH_3)_2C_{12}H_{24}C_6H_5\ Cl^-$" should be -- $(C_4H_8O)_3SiCH_2N^+(CH_3)_2C_{12}H_{24}C_6H_5\ Cl^-$ --.

Column 25, line 25,

"$CH_3O)_3SiCH_2N^+[(C_3H_6O)_3C_2H_5]_2C_8H_{17}\ Cl^-$" should be -- $(CH_3O)_3SiCH_2N^+[(C_3H_6O)_3C_2H_5]_2C_8H_{17}\ Cl^-$ --.

UNITED STATES PATENT AND TRADEMARK OFFICE
CERTIFICATE OF CORRECTION

PATENT NO. : 4,013,573
DATED : March 22, 1977
INVENTOR(S) : John W. Leikhim et al It is certified that error appears in the above-identified patent and that said Letters Patent are hereby corrected as shown below:

Column 25, line 26, please delete.

Column 25, line 33, "$(CH_3O)_2CH_3SiCH(C_{18}H_{37})S^+(CH_3)_2 Br^-$" should be -- $(CH_3O)_2CH_3SiCH(C_{18}H_{37})N^+(CH_3)_3 Br^-$ --.

Column 25, after line 33, please insert -- $(CH_3O)_2CH_3SiCH(C_{18}H_{37})S^+(CH_3)_2 Br^-$ --.

Signed and Sealed this

Sixth Day of June 1978

[SEAL]

Attest:

RUTH C. MASON
*Attesting Officer*

DONALD W. BANNER
*Commissioner of Patents and Trademarks*